(12) United States Patent
Heske et al.

(10) Patent No.: US 8,002,713 B2
(45) Date of Patent: Aug. 23, 2011

(54) BIOPSY DEVICE AND INSERTABLE BIOPSY NEEDLE MODULE

(75) Inventors: Norbert Heske, Kotigeisering (DE); Thomas Heske, Grafrath (DE)

(73) Assignee: C. R. Bard, Inc., Murray Hill, NJ (US)

( * ) Notice: Subject to any disclaimer, the term of this patent is extended or adjusted under 35 U.S.C. 154(b) by 1254 days.

(21) Appl. No.: 10/500,518

(22) PCT Filed: Mar. 5, 2003

(86) PCT No.: PCT/EP03/02285
§ 371 (c)(1),
(2), (4) Date: Mar. 1, 2005

(87) PCT Pub. No.: WO03/077768
PCT Pub. Date: Sep. 25, 2003

(65) Prior Publication Data
US 2005/0165328 A1 Jul. 28, 2005

(30) Foreign Application Priority Data

Mar. 19, 2002 (DE) .................... 102 12 154
Aug. 2, 2002 (DE) .................... 102 35 480
Oct. 17, 2002 (DE) .................... 102 48 425

(51) Int. Cl.
*A61B 10/00* (2006.01)

(52) U.S. Cl. .................... 600/566; 600/565; 600/568
(58) Field of Classification Search .................. 600/565, 600/566, 568, 562, 564, 567
See application file for complete search history.

(56) References Cited

U.S. PATENT DOCUMENTS

| | | |
|---|---|---|
| 33,258 A | 9/1861 | Miller |
| 737,293 A | 8/1903 | Summerfeldt |
| 1,585,934 A | 5/1926 | Muir |
| 1,663,761 A | 3/1928 | Johnson |
| 2,953,934 A | 9/1960 | Sundt |
| 3,019,733 A | 2/1962 | Braid |
| 3,224,434 A | 12/1965 | Molomut et al. |
| 3,477,423 A | 11/1969 | Griffith |
| 3,512,519 A | 5/1970 | Hall |
| 3,561,429 A * | 2/1971 | Jewett et al. .................. 600/565 |
| 3,565,074 A | 2/1971 | Foti |
| 3,606,878 A | 9/1971 | Kellogg, Jr. |
| 3,727,602 A | 4/1973 | Hyden et al. |
| 3,732,858 A | 5/1973 | Banko |
| 3,844,272 A | 10/1974 | Banko |
| 3,882,849 A | 5/1975 | Jamshidi |
| 4,275,730 A | 6/1981 | Hussein |
| 4,282,884 A | 8/1981 | Boebel |
| 4,354,092 A | 10/1982 | Manabe et al. |

(Continued)

FOREIGN PATENT DOCUMENTS

DE 3924291 A1 1/1991

(Continued)

*Primary Examiner* — Max Hindenburg
*Assistant Examiner* — Emily M Lloyd

(57) ABSTRACT

A biopsy device for tissue collection having a housing and a removable element. A power source is contained within the housing and the removable unit includes a biopsy needle module and a pressure source that can be integrated into the housing such that the biopsy device is fully operational without the need for wires or cables extending from the housing to connect to external units. The biopsy needle module includes a biopsy needle and a cutting sleeve, the biopsy needle having a sharpened distal end and a distal opening for collection of tissue, the cutting sleeve having a cutting blade on its distal end and being coaxially positioned with respect to the biopsy needle.

29 Claims, 16 Drawing Sheets

U.S. PATENT DOCUMENTS

| | | | |
|---|---|---|---|
| 4,445,509 A | 5/1984 | Auth | |
| 4,490,137 A | 12/1984 | Moukheibir | |
| 4,549,554 A | 10/1985 | Markham | |
| 4,577,629 A | 3/1986 | Martinez | |
| 4,589,414 A | 5/1986 | Yoshida et al. | |
| 4,603,694 A | 8/1986 | Wheeler | |
| 4,605,011 A * | 8/1986 | Naslund | 600/565 |
| 4,617,430 A | 10/1986 | Bryant | |
| 4,645,153 A | 2/1987 | Granzow et al. | |
| 4,678,459 A | 7/1987 | Onik et al. | |
| 4,696,298 A | 9/1987 | Higgins et al. | |
| 4,702,260 A | 10/1987 | Wang | |
| 4,844,087 A | 7/1989 | Garg | |
| 4,850,354 A | 7/1989 | McGurk-Burleson et al. | |
| 4,893,635 A | 1/1990 | de Groot et al. | |
| 4,907,598 A | 3/1990 | Bauer | |
| RE33,258 E | 7/1990 | Onik et al. | |
| 4,940,061 A | 7/1990 | Terwilliger et al. | |
| 4,958,625 A | 9/1990 | Bates et al. | |
| 4,967,762 A | 11/1990 | DeVries | |
| 4,986,278 A | 1/1991 | Ravid et al. | |
| 4,986,279 A | 1/1991 | O'Neill | |
| 4,986,807 A | 1/1991 | Farr | |
| 4,989,614 A * | 2/1991 | Dejter et al. | 600/565 |
| 5,025,797 A | 6/1991 | Baran | |
| 5,125,413 A | 6/1992 | Baran | |
| 5,138,245 A | 8/1992 | Mattinger et al. | |
| 5,158,528 A | 10/1992 | Walker et al. | |
| 5,176,628 A | 1/1993 | Charles et al. | |
| 5,225,763 A | 7/1993 | Krohn et al. | |
| 5,234,000 A | 8/1993 | Hakky et al. | |
| 5,236,334 A | 8/1993 | Bennett | |
| 5,282,476 A | 2/1994 | Terwilliger | |
| 5,282,477 A | 2/1994 | Bauer | |
| 5,324,306 A | 6/1994 | Makower et al. | |
| 5,334,183 A | 8/1994 | Wuchinich | |
| 5,368,029 A | 11/1994 | Holcombe et al. | |
| 5,368,045 A | 11/1994 | Bates et al. | |
| 5,400,798 A | 3/1995 | Baran | |
| 5,439,474 A | 8/1995 | Li | |
| 5,458,112 A | 10/1995 | Weaver | |
| 5,479,486 A | 12/1995 | Saji | |
| 5,485,917 A | 1/1996 | Early | |
| 5,492,130 A | 2/1996 | Chiou | |
| 5,496,860 A | 3/1996 | Matsumoto et al. | |
| 5,511,556 A | 4/1996 | DeSantis | |
| 5,526,822 A | 6/1996 | Burbank et al. | |
| 5,535,755 A | 7/1996 | Heske | |
| 5,546,957 A | 8/1996 | Heske | |
| 5,554,151 A | 9/1996 | Hinchliffe | |
| 5,560,373 A | 10/1996 | De Santis | |
| 5,564,436 A | 10/1996 | Hakky et al. | |
| 5,569,284 A | 10/1996 | Young et al. | |
| 5,601,585 A | 2/1997 | Banik et al. | |
| 5,602,449 A | 2/1997 | Krause et al. | |
| 5,617,874 A | 4/1997 | Baran | |
| 5,649,547 A | 7/1997 | Ritchart et al. | |
| 5,655,542 A | 8/1997 | Weilandt | |
| 5,655,657 A | 8/1997 | Roshdy | |
| 5,665,101 A | 9/1997 | Becker et al. | |
| 5,699,909 A | 12/1997 | Foster | |
| 5,709,697 A | 1/1998 | Ratcliff et al. | |
| 5,720,760 A | 2/1998 | Becker et al. | |
| 5,735,264 A | 4/1998 | Siczek et al. | |
| 5,752,923 A | 5/1998 | Terwilliger | |
| 5,755,714 A | 5/1998 | Murphy-Chutorian | |
| 5,766,135 A | 6/1998 | Terwilliger | |
| 5,769,086 A | 6/1998 | Ritchart et al. | |
| 5,769,795 A | 6/1998 | Terwilliger | |
| 5,775,333 A | 7/1998 | Burbank et al. | |
| 5,788,651 A | 8/1998 | Weilandt | |
| 5,792,167 A | 8/1998 | Kablik et al. | |
| 5,807,282 A | 9/1998 | Fowler | |
| 5,817,033 A | 10/1998 | DeSantis et al. | |
| 5,817,034 A | 10/1998 | Milliman et al. | |
| 5,823,970 A | 10/1998 | Terwilliger | |
| 5,830,219 A | 11/1998 | Bird et al. | |
| D403,405 S | 12/1998 | Terwilliger | |
| 5,857,982 A | 1/1999 | Milliman et al. | |
| 5,908,233 A | 6/1999 | Heskett et al. | |
| 5,913,857 A | 6/1999 | Ritchart et al. | |
| 5,916,229 A | 6/1999 | Evans | |
| 5,928,164 A | 7/1999 | Burbank et al. | |
| 5,944,673 A | 8/1999 | Gregoire et al. | |
| 5,951,490 A | 9/1999 | Fowler | |
| 5,951,575 A | 9/1999 | Bolduc et al. | |
| 5,964,716 A * | 10/1999 | Gregoire et al. | 600/566 |
| 5,971,939 A | 10/1999 | Cooper et al. | |
| 5,976,164 A | 11/1999 | Mueller et al. | |
| 5,980,469 A | 11/1999 | Burbank et al. | |
| 6,007,495 A | 12/1999 | Matula | |
| 6,007,497 A | 12/1999 | Huitema | |
| 6,007,556 A | 12/1999 | Kablik et al. | |
| 6,017,316 A | 1/2000 | Ritchart et al. | |
| 6,018,227 A | 1/2000 | Kumar et al. | |
| 6,019,733 A | 2/2000 | Farascioni | |
| 6,022,324 A | 2/2000 | Skinner | |
| 6,022,325 A | 2/2000 | Siczek et al. | |
| 6,027,458 A | 2/2000 | Janssens | |
| 6,036,657 A | 3/2000 | Milliman et al. | |
| 6,050,955 A | 4/2000 | Bryan et al. | |
| 6,077,230 A | 6/2000 | Gregoire et al. | |
| 6,083,176 A | 7/2000 | Terwilliger | |
| 6,083,237 A | 7/2000 | Huitema et al. | |
| 6,086,544 A | 7/2000 | Hibner et al. | |
| 6,106,484 A | 8/2000 | Terwilliger | |
| 6,110,129 A | 8/2000 | Terwilliger | |
| 6,120,462 A | 9/2000 | Hibner et al. | |
| 6,123,957 A | 9/2000 | Jernberg | |
| 6,126,617 A | 10/2000 | Weilandt et al. | |
| 6,142,955 A | 11/2000 | Klecher et al. | |
| 6,162,187 A | 12/2000 | Buzzard et al. | |
| 6,165,136 A | 12/2000 | Nishtala | |
| 6,193,673 B1 | 2/2001 | Viola et al. | |
| 6,196,978 B1 | 3/2001 | Weilandt et al. | |
| 6,213,957 B1 | 4/2001 | Milliman et al. | |
| 6,220,248 B1 | 4/2001 | Voegele et al. | |
| 6,231,522 B1 | 5/2001 | Voegele et al. | |
| 6,241,687 B1 | 6/2001 | Voegele et al. | |
| 6,273,861 B1 | 8/2001 | Bates et al. | |
| 6,273,862 B1 | 8/2001 | Privitera et al. | |
| 6,280,398 B1 | 8/2001 | Ritchart et al. | |
| 6,283,925 B1 | 9/2001 | Terwilliger | |
| 6,322,523 B2 | 11/2001 | Weilandt et al. | |
| 6,328,701 B1 | 12/2001 | Terwilliger | |
| 6,331,166 B1 | 12/2001 | Burbank et al. | |
| 6,358,217 B1 | 3/2002 | Bourassa | |
| 6,402,701 B1 | 6/2002 | Kaplan et al. | |
| 6,419,641 B1 | 7/2002 | Mark et al. | |
| 6,428,486 B2 | 8/2002 | Ritchart et al. | |
| 6,428,487 B1 | 8/2002 | Burdorff et al. | |
| 6,432,064 B1 | 8/2002 | Hibner et al. | |
| 6,432,065 B1 | 8/2002 | Burdorff et al. | |
| 6,436,054 B1 | 8/2002 | Viola et al. | |
| 6,482,158 B2 | 11/2002 | Mault | |
| 6,485,436 B1 | 11/2002 | Truckai et al. | |
| 6,488,636 B2 | 12/2002 | Bryan et al. | |
| 6,527,736 B1 | 3/2003 | Attinger et al. | |
| 6,540,694 B1 | 4/2003 | Van Bladel et al. | |
| 6,540,761 B2 | 4/2003 | Houser | |
| 6,551,255 B2 | 4/2003 | Van Bladel et al. | |
| 6,554,779 B2 | 4/2003 | Viola et al. | |
| 6,585,664 B2 | 7/2003 | Burdorff et al. | |
| 6,638,235 B2 | 10/2003 | Miller et al. | |
| 6,659,105 B2 | 12/2003 | Burbank et al. | |
| 6,659,338 B1 | 12/2003 | Dittmann et al. | |
| 6,683,439 B2 | 1/2004 | Takano et al. | |
| 6,689,072 B2 | 2/2004 | Kaplan et al. | |
| 6,695,786 B2 | 2/2004 | Wang et al. | |
| 6,712,774 B2 | 3/2004 | Voegele et al. | |
| 6,752,768 B2 | 6/2004 | Burdorff et al. | |
| 6,753,671 B1 | 6/2004 | Harvey | |
| 6,758,824 B1 | 7/2004 | Miller et al. | |
| 6,764,495 B2 | 7/2004 | Lee et al. | |
| 6,832,990 B2 | 12/2004 | Kortenbach et al. | |
| 6,849,080 B2 | 2/2005 | Lee et al. | |
| D508,458 S | 8/2005 | Solland et al. | |

| | | |
|---|---|---|
| 6,926,676 B2 | 8/2005 | Turturro et al. |
| 6,984,213 B2 | 1/2006 | Horner et al. |
| 7,025,732 B2 | 4/2006 | Thompson et al. |
| D525,583 S | 7/2006 | Vu |
| 7,153,274 B2 | 12/2006 | Stephens et al. |
| 7,189,206 B2 | 3/2007 | Quick et al. |
| 7,219,867 B2 | 5/2007 | Kalis et al. |
| 7,226,424 B2 | 6/2007 | Ritchart et al. |
| 7,276,032 B2 | 10/2007 | Hibner |
| 7,328,794 B2 | 2/2008 | Lubs et al. |
| 7,347,829 B2 | 3/2008 | Mark et al. |
| 7,374,544 B2 | 5/2008 | Freeman et al. |
| 7,397,654 B2 | 7/2008 | Mori |
| 7,402,140 B2 | 7/2008 | Spero et al. |
| 7,405,536 B2 | 7/2008 | Watts |
| 7,407,054 B2 | 8/2008 | Seiler et al. |
| 7,432,813 B2 | 10/2008 | Postma |
| 7,452,367 B2 | 11/2008 | Rassman et al. |
| 7,464,040 B2 | 12/2008 | Joao |
| 7,490,048 B2 | 2/2009 | Joao |
| 7,648,466 B2 | 1/2010 | Stephens et al. |
| 2001/0007925 A1 | 7/2001 | Ritchart et al. |
| 2001/0011156 A1 | 8/2001 | Viola et al. |
| 2001/0012919 A1 | 8/2001 | Terwilliger |
| 2001/0014779 A1 | 8/2001 | Lubock et al. |
| 2001/0034530 A1 | 10/2001 | Malackowski et al. |
| 2001/0044595 A1 | 11/2001 | Reydel et al. |
| 2001/0047183 A1 | 11/2001 | Privitera et al. |
| 2002/0016555 A1 | 2/2002 | Ritchart et al. |
| 2002/0045840 A1 | 4/2002 | Voegele et al. |
| 2002/0045842 A1 | 4/2002 | Van Bladel et al. |
| 2002/0065474 A1 | 5/2002 | Viola |
| 2002/0067151 A1 | 6/2002 | Tanishita |
| 2002/0068878 A1 | 6/2002 | Jassoni et al. |
| 2002/0082518 A1 | 6/2002 | Weiss et al. |
| 2002/0082519 A1 | 6/2002 | Miller et al. |
| 2002/0107043 A1 | 8/2002 | Adamson et al. |
| 2002/0120212 A1 | 8/2002 | Ritchart et al. |
| 2002/0151822 A1 | 10/2002 | Burdoff et al. |
| 2002/0156395 A1 | 10/2002 | Stephens et al. |
| 2003/0130593 A1 | 7/2003 | Gonzalez |
| 2003/0130677 A1 | 7/2003 | Whitman et al. |
| 2003/0163142 A1 | 8/2003 | Paltieli et al. |
| 2003/0229293 A1 | 12/2003 | Hibner et al. |
| 2003/0233101 A1 | 12/2003 | Lubock et al. |
| 2004/0015079 A1 | 1/2004 | Berger et al. |
| 2004/0019297 A1 | 1/2004 | Angel |
| 2004/0030367 A1 | 2/2004 | Yamaki et al. |
| 2004/0049128 A1 | 3/2004 | Miller et al. |
| 2004/0186393 A1 | 9/2004 | Leigh et al. |
| 2004/0215103 A1 | 10/2004 | Mueller, Jr. et al. |
| 2004/0249278 A1 | 12/2004 | Krause |
| 2004/0249307 A1 | 12/2004 | Thompson et al. |
| 2004/0267157 A1 | 12/2004 | Miller et al. |
| 2005/0004492 A1 | 1/2005 | Burbank et al. |
| 2005/0004559 A1 | 1/2005 | Quick et al. |
| 2005/0010131 A1 | 1/2005 | Burbank et al. |
| 2005/0020909 A1 | 1/2005 | Moctezuma de la Barrera et al. |
| 2005/0027210 A1 | 2/2005 | Miller |
| 2005/0049489 A1 | 3/2005 | Foerster et al. |
| 2005/0049521 A1 | 3/2005 | Miller et al. |
| 2005/0080355 A1 | 4/2005 | Mark |
| 2005/0085838 A1 | 4/2005 | Thompson et al. |
| 2005/0113715 A1 | 5/2005 | Schwindt et al. |
| 2005/0113716 A1 | 5/2005 | Mueller, Jr. et al. |
| 2005/0124914 A1 | 6/2005 | Dicarlo et al. |
| 2005/0124915 A1 | 6/2005 | Eggers et al. |
| 2005/0177117 A1 | 8/2005 | Crocker et al. |
| 2005/0193451 A1 | 9/2005 | Quistgaard et al. |
| 2005/0203439 A1 | 9/2005 | Heske et al. |
| 2005/0209530 A1 | 9/2005 | Pflueger |
| 2005/0275378 A1 | 12/2005 | Canino et al. |
| 2005/0277829 A1 | 12/2005 | Tsonton et al. |
| 2005/0277871 A1 | 12/2005 | Selis |
| 2006/0030784 A1 | 2/2006 | Miller et al. |
| 2006/0113958 A1 | 6/2006 | Lobert et al. |
| 2006/0116603 A1 | 6/2006 | Shibazaki et al. |
| 2006/0129063 A1 | 6/2006 | Thompson et al. |
| 2006/0178666 A1 | 8/2006 | Cosman et al. |
| 2006/0184063 A1 | 8/2006 | Miller |
| 2006/0258956 A1 | 11/2006 | Haberstich et al. |
| 2007/0016101 A1 | 1/2007 | Feldman et al. |
| 2007/0027407 A1 | 2/2007 | Miller |
| 2007/0032741 A1 | 2/2007 | Hibner et al. |
| 2007/0073326 A1 | 3/2007 | Miller et al. |
| 2007/0090788 A1 | 4/2007 | Hansford et al. |
| 2007/0106176 A1 | 5/2007 | Mark et al. |
| 2007/0118049 A1 | 5/2007 | Viola |
| 2007/0149894 A1 | 6/2007 | Heske et al. |
| 2007/0161925 A1 | 7/2007 | Quick et al. |
| 2007/0167782 A1 | 7/2007 | Callahan et al. |
| 2007/0213590 A1 | 9/2007 | Squicciarini |
| 2007/0213630 A1 | 9/2007 | Beckman et al. |
| 2007/0213632 A1 | 9/2007 | Okazaki et al. |
| 2007/0236180 A1 | 10/2007 | Rodgers |
| 2007/0239067 A1 | 10/2007 | Hibner et al. |
| 2007/0255173 A1 | 11/2007 | Hibner |
| 2007/0270710 A1 | 11/2007 | Frass et al. |
| 2007/0276288 A1 | 11/2007 | Khaw |
| 2007/0287933 A1 | 12/2007 | Phan et al. |
| 2007/0293788 A1 | 12/2007 | Entrekin et al. |
| 2008/0004545 A1 | 1/2008 | Garrison |
| 2008/0007217 A1 | 1/2008 | Riley |
| 2008/0015429 A1 | 1/2008 | Tsonton et al. |
| 2008/0021487 A1 | 1/2008 | Heisler |
| 2008/0021488 A1 | 1/2008 | Berberich |
| 2008/0030170 A1 | 2/2008 | Dacquay et al. |
| 2008/0064925 A1 | 3/2008 | Gill et al. |
| 2008/0064984 A1 | 3/2008 | Pflueger |
| 2008/0079391 A1 | 4/2008 | Schroeck et al. |
| 2008/0110261 A1 | 5/2008 | Randall et al. |
| 2008/0135443 A1 | 6/2008 | Frojd et al. |
| 2008/0146962 A1 | 6/2008 | Ritchie et al. |
| 2008/0154151 A1 | 6/2008 | Ritchart et al. |
| 2008/0161682 A1 | 7/2008 | Kendrick et al. |
| 2008/0161718 A1 | 7/2008 | Schwindt |
| 2008/0161719 A1 | 7/2008 | Miller et al. |
| 2008/0161720 A1 | 7/2008 | Nicoson et al. |
| 2008/0183099 A1 | 7/2008 | Jorgensen et al. |
| 2008/0195066 A1 | 8/2008 | Speeg et al. |
| 2008/0200833 A1 | 8/2008 | Hardin et al. |
| 2008/0200836 A1 | 8/2008 | Speeg et al. |
| 2008/0208194 A1 | 8/2008 | Bickenbach |
| 2008/0215056 A1 | 9/2008 | Miller et al. |
| 2008/0221443 A1 | 9/2008 | Ritchie et al. |
| 2008/0221444 A1 | 9/2008 | Ritchie et al. |
| 2008/0221478 A1 | 9/2008 | Ritchie et al. |
| 2008/0221479 A1 | 9/2008 | Ritchie et al. |
| 2008/0221480 A1 | 9/2008 | Hibner et al. |
| 2008/0228104 A1 | 9/2008 | Uber et al. |
| 2008/0232604 A1 | 9/2008 | Dufresne et al. |
| 2008/0234715 A1 | 9/2008 | Pesce et al. |
| 2008/0281225 A1 | 11/2008 | Spero et al. |
| 2008/0306406 A1 | 12/2008 | Thompson et al. |
| 2008/0319341 A1 | 12/2008 | Taylor et al. |
| 2009/0030405 A1 | 1/2009 | Quick et al. |
| 2009/0062624 A1 | 3/2009 | Neville |
| 2009/0082695 A1 | 3/2009 | Whitehead |
| 2009/0125062 A1 | 5/2009 | Arnin |
| 2009/0227893 A1 | 9/2009 | Coonahan et al. |

FOREIGN PATENT DOCUMENTS

| | | |
|---|---|---|
| DE | 4041614 C1 | 10/1992 |
| DE | 10034297 A1 | 4/2001 |
| DE | 10026303 A1 | 2/2002 |
| DE | 20204363 U1 | 5/2002 |
| DE | 20204362 U1 | 7/2002 |
| DE | 20211934 U1 | 9/2002 |
| DE | 20209525 U1 | 11/2002 |
| DE | 10235480 A1 | 2/2004 |
| EP | 0433717 A1 | 6/1991 |
| EP | 0890 339 | 1/1999 |
| EP | 0 995 400 A1 | 4/2000 |
| EP | 1074271 | 2/2001 |
| EP | 1520518 A2 | 4/2005 |
| EP | 1579809 A1 | 9/2005 |
| EP | 1665989 A2 | 6/2006 |
| FR | 1345429 A | 12/1963 |

| | | | |
|---|---|---|---|
| FR | 2739293 A1 | 4/1997 |
| GB | 2018601 | 10/1979 |
| WO | WO 96/28097 | 9/1996 |
| WO | WO 98/25522 | 6/1998 |
| WO | 9831285 A1 | 7/1998 |
| WO | 9835615 A1 | 8/1998 |
| WO | 9846290 A1 | 10/1998 |
| WO | 9933501 A1 | 7/1999 |
| WO | WO 00/30546 | 6/2000 |
| WO | WO 00/59378 | 10/2000 |
| WO | 0172230 A1 | 10/2001 |
| WO | 0222023 A1 | 3/2002 |
| WO | WO 02/32318 A1 | 4/2002 |
| WO | WO 02/069808 A2 | 9/2002 |
| WO | 2005013830 A1 | 2/2005 |
| WO | 2006015302 A1 | 2/2006 |
| WO | 2007095330 A2 | 8/2007 |
| WO | 2007112751 A2 | 10/2007 |
| WO | 2008021687 A1 | 2/2008 |
| WO | 2008040812 A1 | 4/2008 |

* cited by examiner

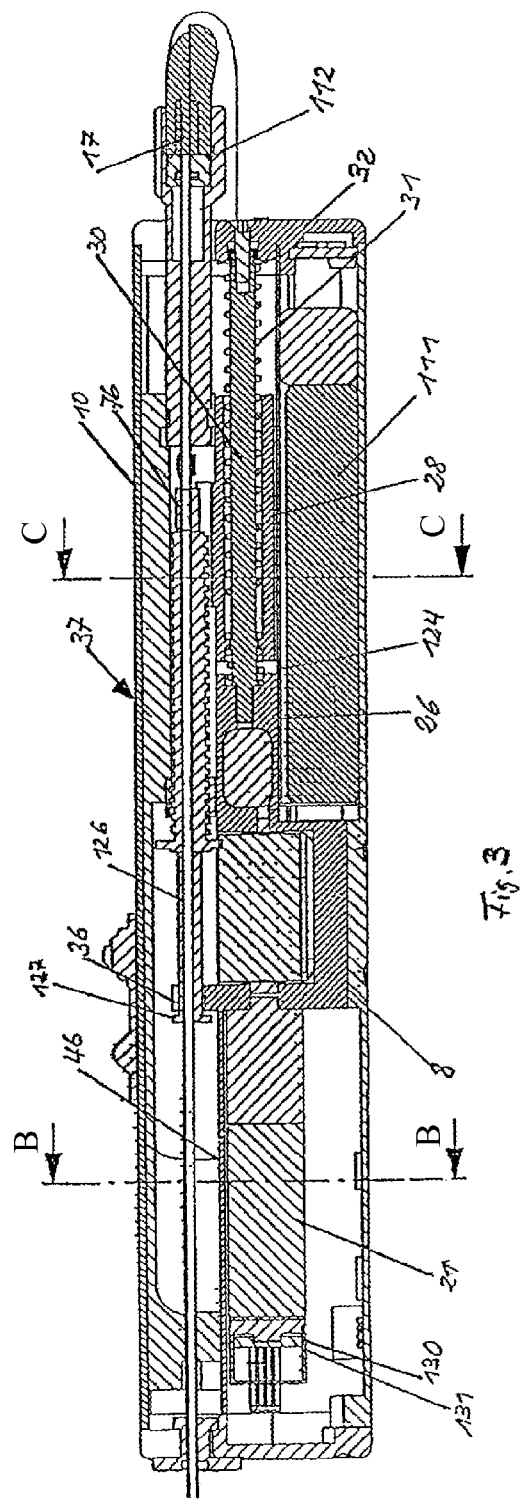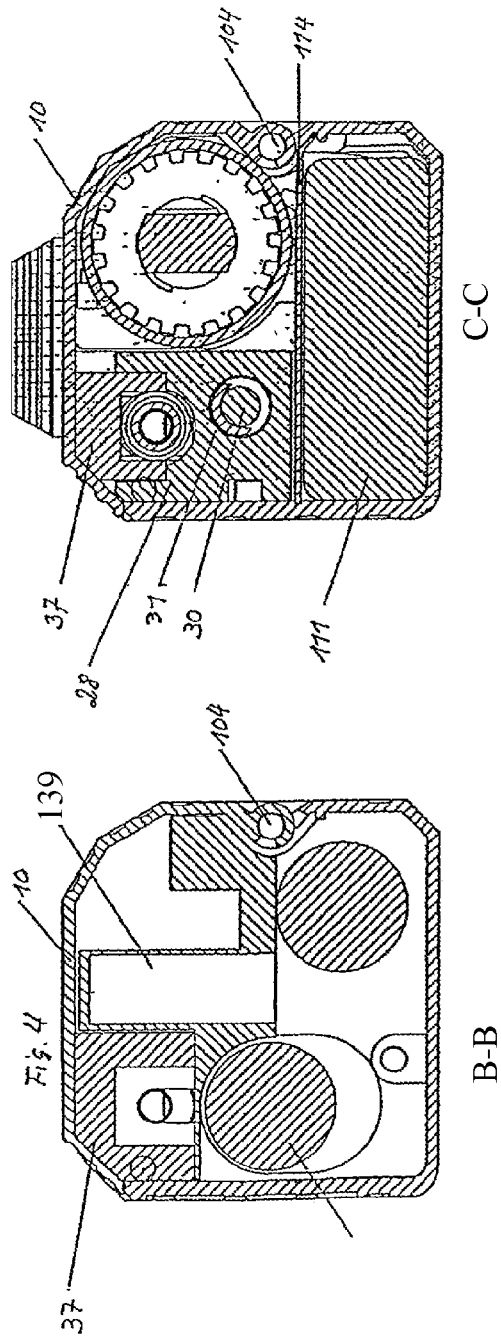

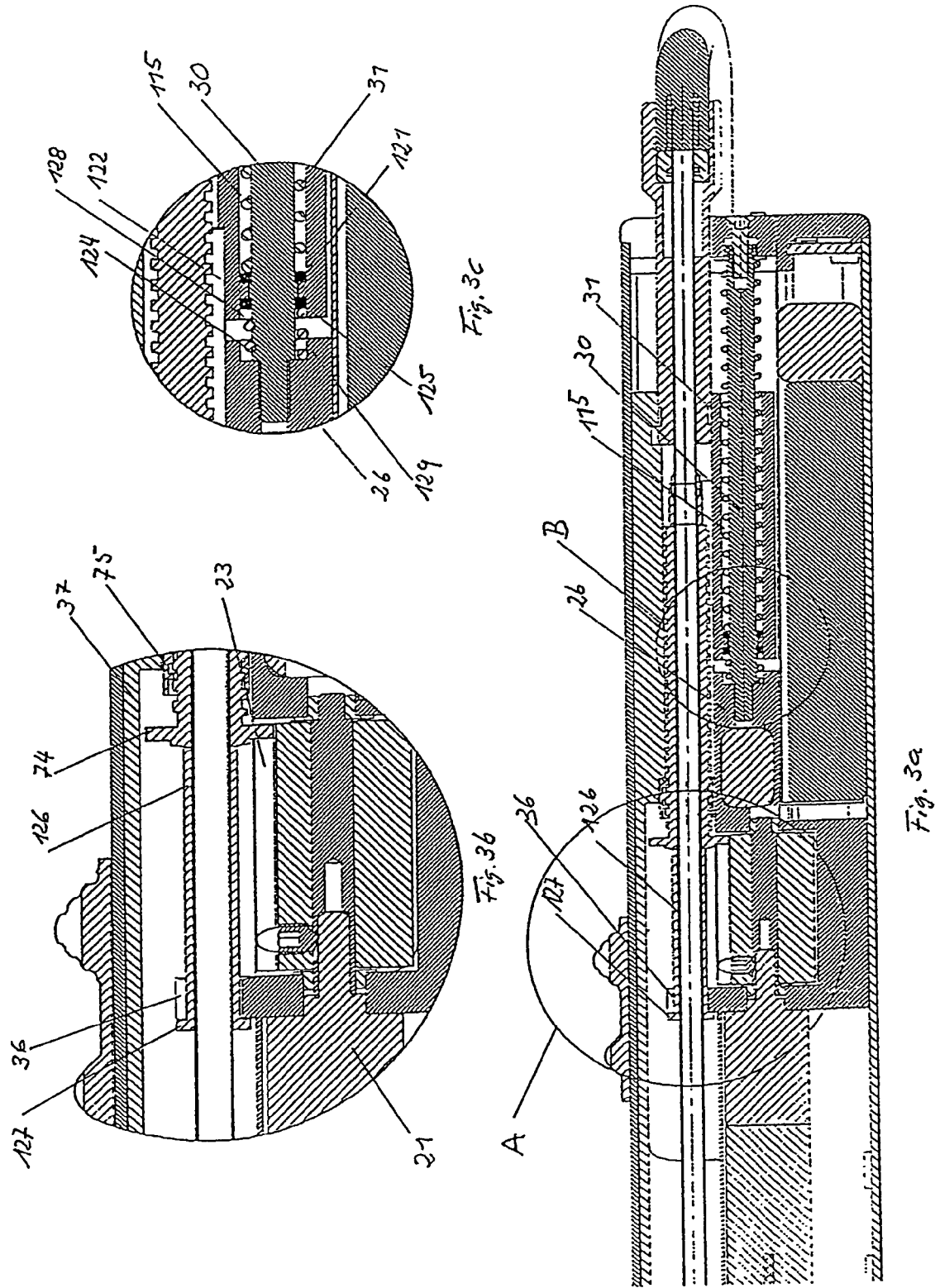

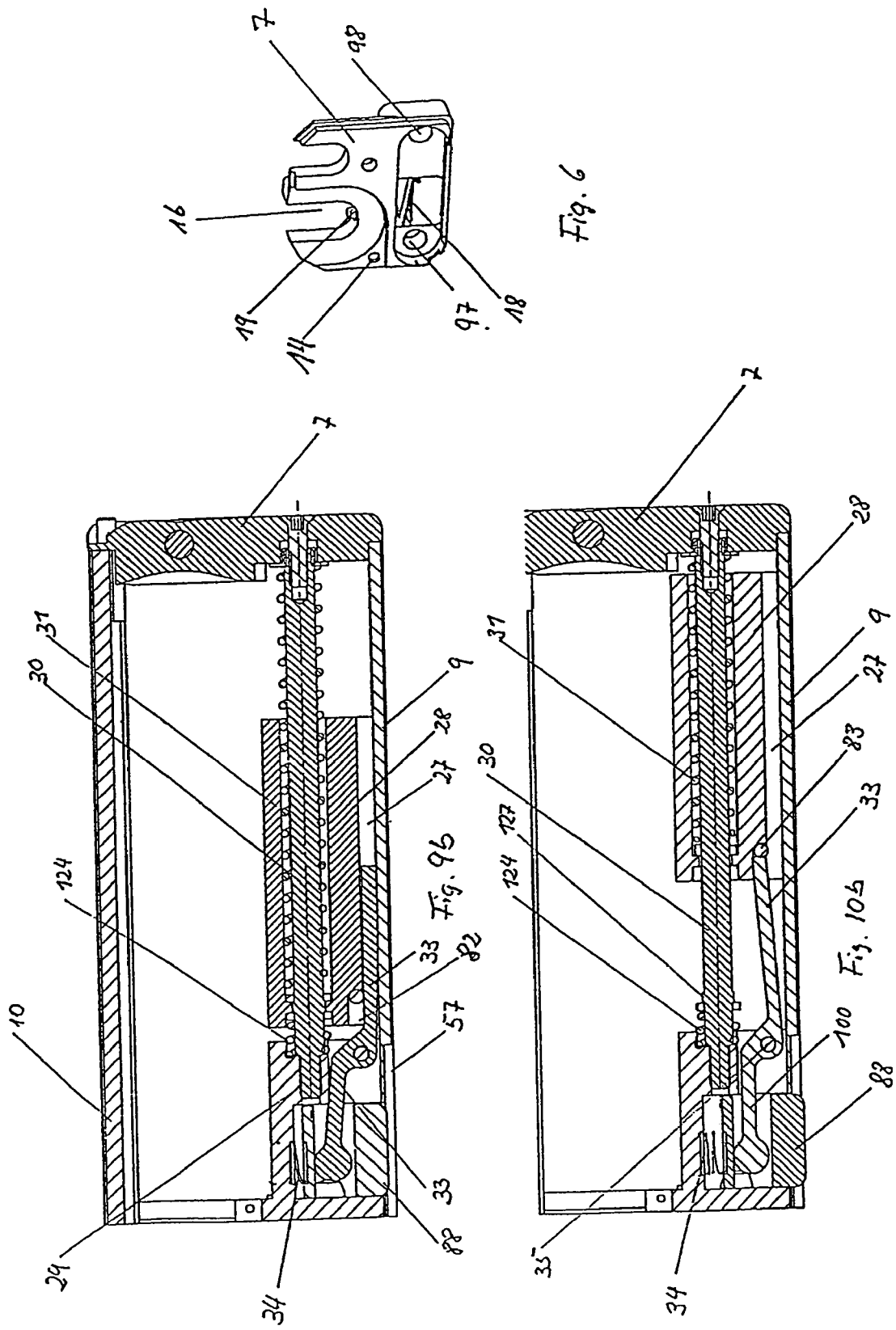

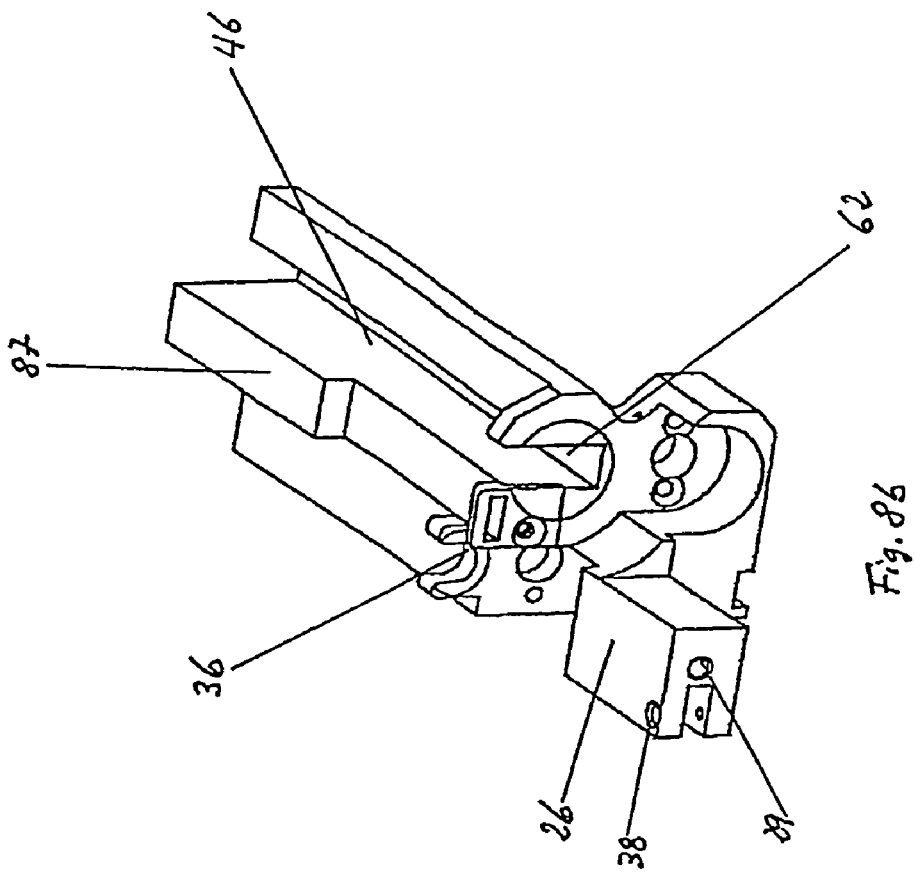
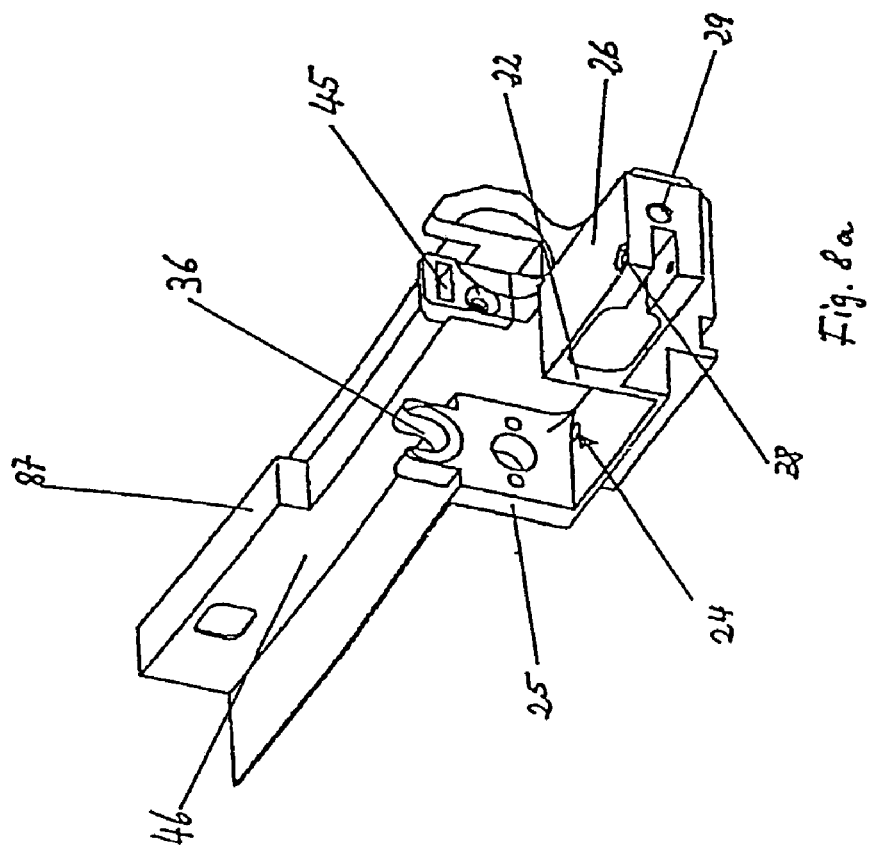

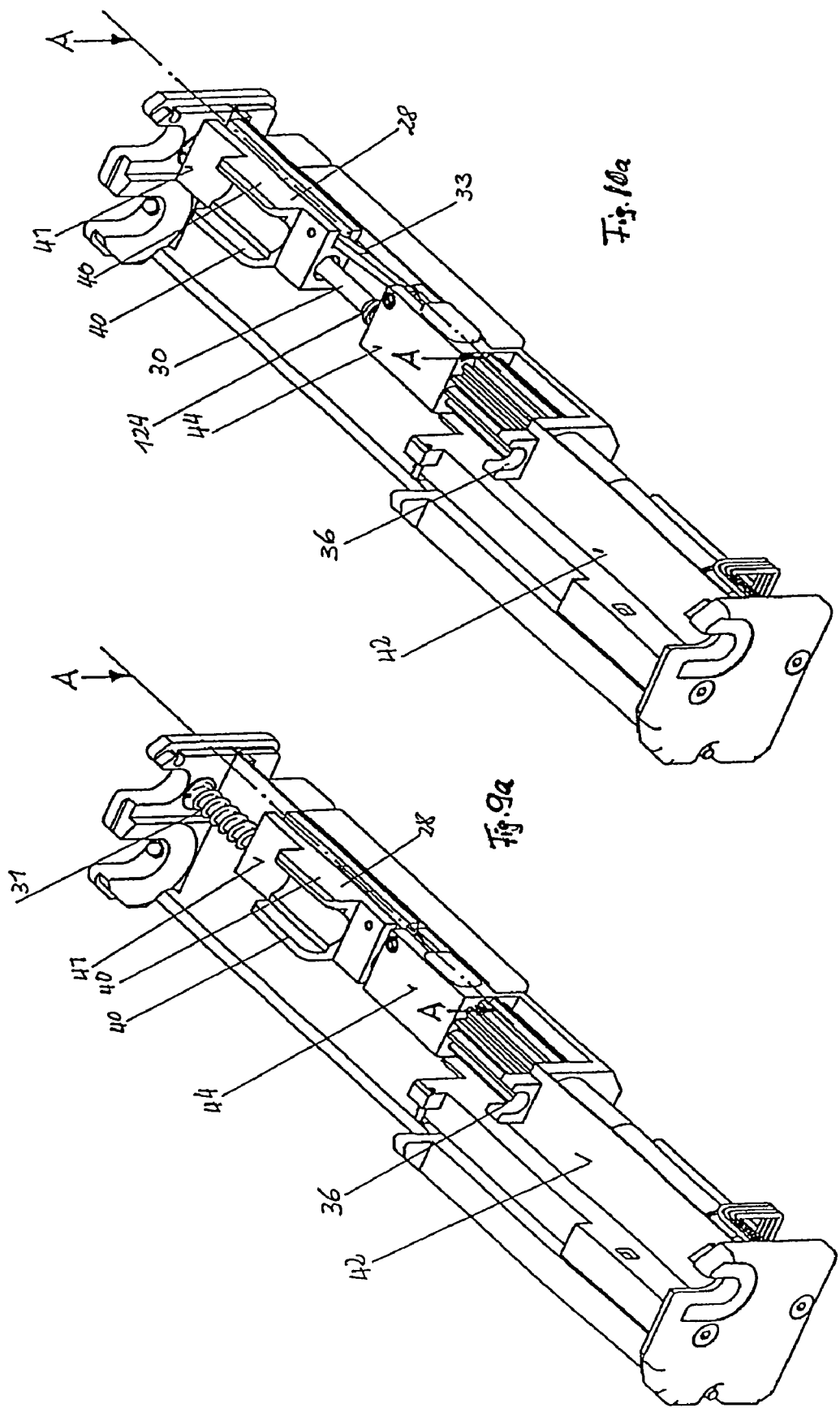

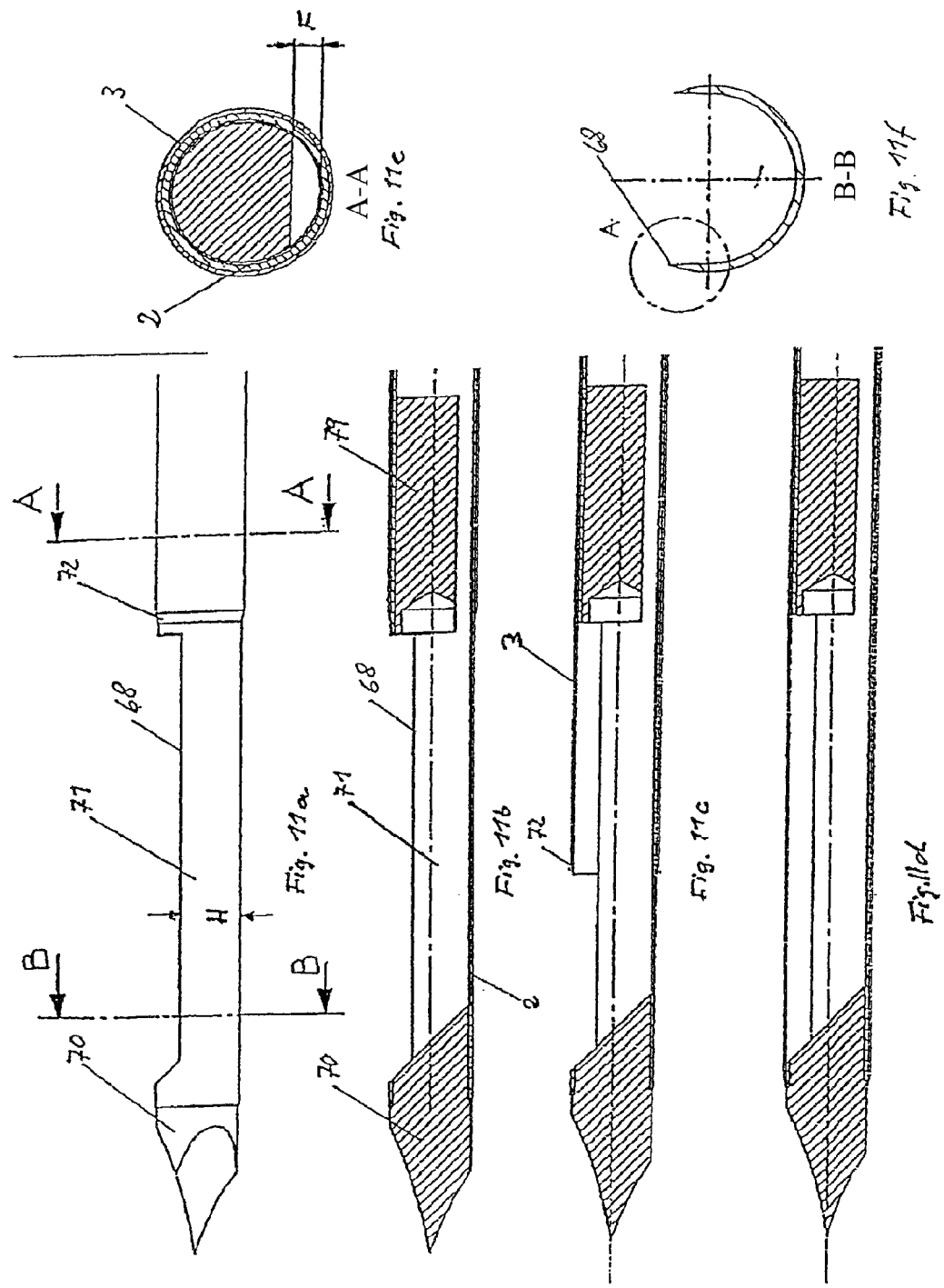

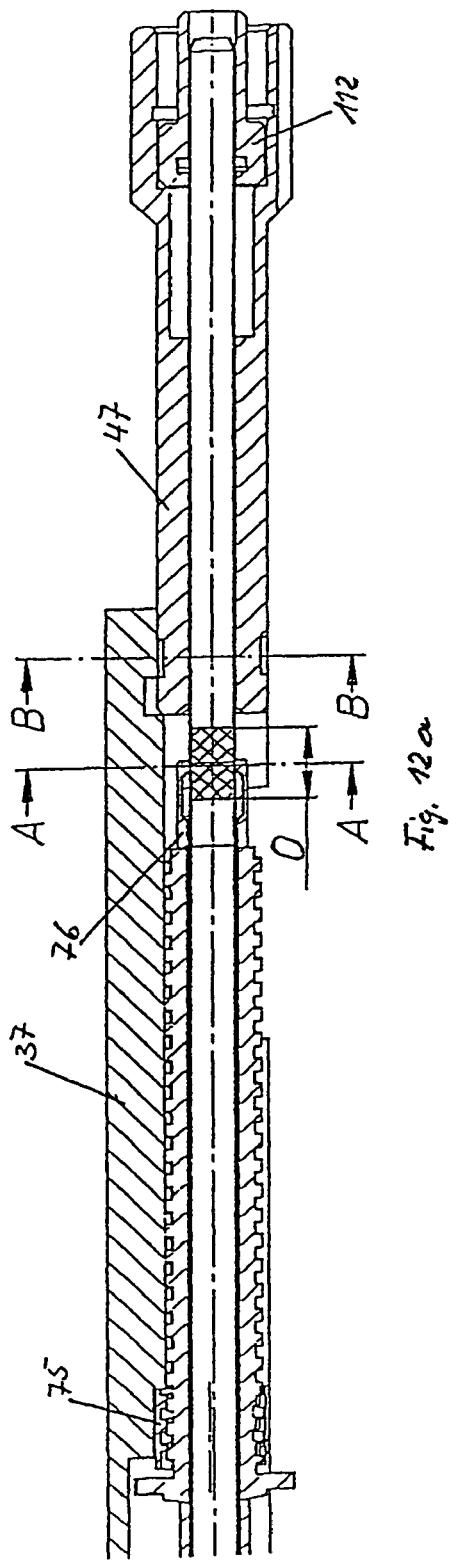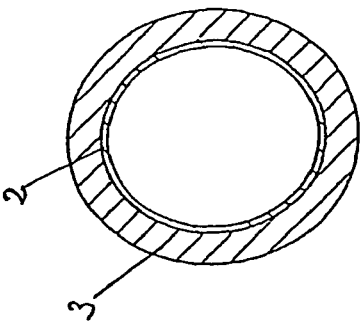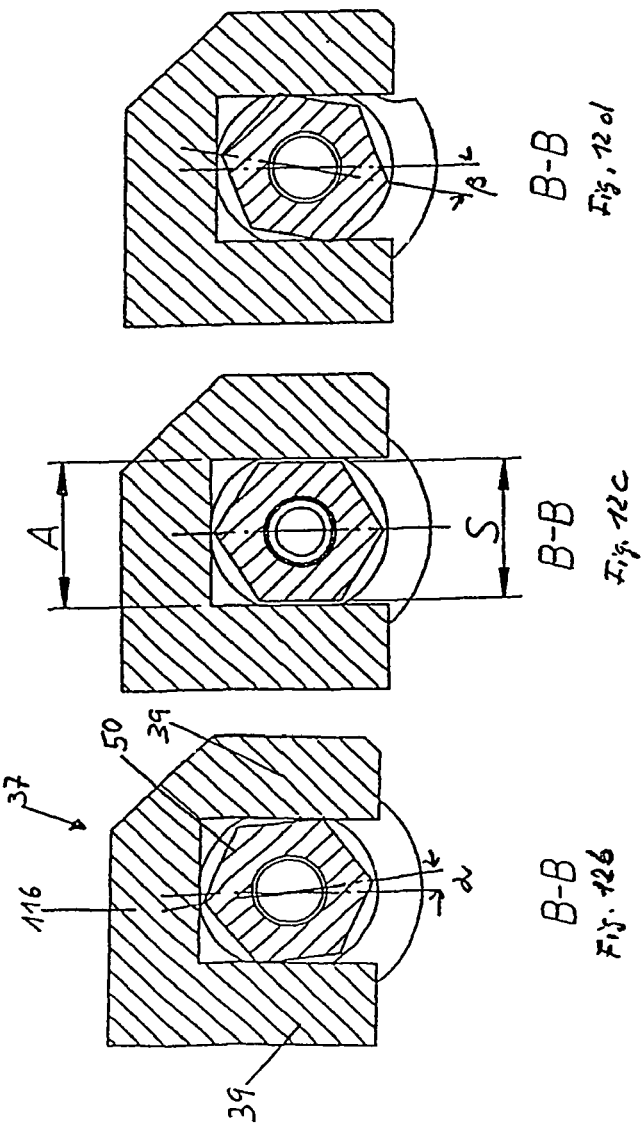

BIOPSY DEVICE AND INSERTABLE BIOPSY NEEDLE MODULE

CROSS-REFERENCE TO RELATED APPLICATIONS

This is a national stage application under 35 USC §371 of International Application PCT/EP03/02285, filed on Mar. 5, 2003, the entire contents of which are incorporated by reference herein.

FIELD OF THE INVENTION

The invention relates to a biopsy device for tissue removal in the form of a manual component with at least one elastic force-actuated clamping cradle for a biopsy needle unit, which features an outer hollow needle with a distally sharpened cutting blade and a hollow biopsy needle mounted in the interior of the hollow needle with a tissue sample removal chamber provided in its distal end region, wherein the outer hollow needle is slidably seated relative to the hollow biopsy needle, as well as with a pressure source connectable to the hollow biopsy needle. A biopsy needle module suitable for operation of the biopsy device is also described.

BACKGROUND OF THE INVENTION

German Patent No. DE 40 41 614 C1 discloses a suction biopsy device, which is designed as a manual device and possesses a vacuum source and a biopsy cannula connector, which can be rotated by means of a rotation drive connected via a flexible shaft. A biopsy cannula designed as a hollow cannula can be connected to the biopsy cannula connector, and said biopsy cannula preferably features a circumferential, sharpened cutting edge at its distal end, along the hollow channel of which a vacuum can be applied by means of the vacuum source, which is designed as a piston-cylinder unit, as soon as the hollow cannula has been positioned at a specific intracorporal tissue location.

International Publication No. WO 96/28097 discloses a similar vacuum-supported biopsy device which, although it does not provide for a rotatable hollow cannula, does feature a syringe piston arrangement for generating a vacuum and disposed inside a manual device.

German Publication No. DE 100 34 297 A1 describes, in contrast to the preceding suction biopsy devices with only one hollow needle, a tissue removal endoscopy instrument possessing a biopsy needle arrangement, which features a circumferentially sharpened hollow needle at its distal end and a hollow biopsy needle disposed inside the hollow needle, wherein the internally disposed biopsy needle features at its distal end a depression for removal of tissue samples. A suction instrument for generating a vacuum is disposed on the proximal end of the hollow biopsy needle. Tissue is removed by pushing the biopsy needle arrangement in a shared position into a tissue region to be examined, wherein the biopsy needle features a distal tip, which slightly protrudes from the hollow needle at its distal end, so as to facilitate penetration of the biopsy needle arrangement into the tissue, on the one hand, and to prevent penetration of tissue into the interior of the hollow needle, on the other.

When the biopsy needle arrangement is suitably positioned inside the tissue, the hollow needle is pulled a predetermined distance in a proximal direction, wherein the internally disposed biopsy cannula remains in its position and the depression is exposed. The vacuum applied along the biopsy needle results in an active lowering and/or pulling in of surrounding tissue fragments into the depression. When the distal end of the hollow needle with its sharpened distal end is pushed forward over the biopsy needle in controlled manner, a tissue fragment is severed and enclosed within the depression in the biopsy needle. When the entire biopsy needle arrangement is pulled back, the severed tissue sample is removed from the body for examination purposes. The entire tissue removal process described above is performed in such a way that the needle movements and the vacuum application can be performed manually, individually and separate from one another.

In contrast, the biopsy needle arrangement described in International Publication No. WO 98/25522 permits a relative motion, actuated by elastic force, between the internally disposed hollow biopsy needle and the outer hollow needle enclosing the biopsy needle. In this case, the biopsy needle is also positioned at the distal end of the sharpened distal tip of the hollow needle, wherein a vacuum source is provided to supply a targeted vacuum through the hollow biopsy needle and into the region of its depression and supports the tissue intake process. The process of positioning the biopsy needle relative to and, ultimately, inside the tissue region to be examined is exclusively manual. This type of positioning, especially when examining hard tissue regions, produces only unsatisfactory biopsy results.

Similar vacuum-supported tissue removal devices are, moreover, disclosed by British Patent Publication No. GB 2 018 601 A and European Patent Publication No. EP 0 890 399 A1. In these cases, however, the vacuum sources, as well as other control units needed to guide the biopsy needle in a controlled manner, are designed and featured as external auxiliary units to be connected to the biopsy needle arrangement. US Publication No 2001/0011156 A1 also describes a vacuum-supported biopsy device comprising a compactly designed hand-held device, the housing of which contains all drive elements necessary for the needle drive of the biopsy needle arrangement. However, a vacuum source separate from the hand-held device is provided which is connectable by means of a corresponding supply line to the needle arrangement inside the hand-held device at a suitable connection point.

SUMMARY OF THE INVENTION

Commencing with a biopsy needle arrangement according to International Publication No. WO 98/25522, which is viewed as the most relevant state of the art, the underlying objective of the invention is to further develop a biopsy device for tissue removal, which is designed in the form of a hand-held device and features at least one elastic force-actuated clamping and shooting device in the form of a clamping cradle for a biopsy needle unit which features an outer hollow needle with a distally sharpened cutting blade as well as a hollow biopsy needle seated inside the hollow needle with a tissue sample removal chamber at its distal end region, wherein the outer hollow needle is slidably seated relative to the hollow biopsy needle, and which features a vacuum source connectable with the hollow biopsy needle, in such a way that ease of operation of the biopsy device is optimized to such an extent that improved examination of tumors can be guaranteed, in that the size and structure of the tissue sample removable with the biopsy device is such that it provides a pathologist with an excellent basis for further histological examination. In addition, an objective of the invention is to improve the tissue removal process itself. Specifically, this means that the needle movements of the biopsy needle unit required for the tissue severing process and the generation of pressure for targeted development of a vacuum must be precisely matched to one another. An essentially manual matching of needle movements to vacuum generation, as in the case of International Publication No. WO 98/25522, is to be avoided.

In the interest of improving ease of operation, the biopsy device should also feature as a compact a design as possible and, as a hand-held device, should allow for easily moveable single-hand operation, if necessary, so that a single operator can perform the tissue removal process with one hand. In the same vein, the biopsy device should be designed as an autonomously operating hand-held instrument, the operation of which does not require any external control or supply units that would require connecting lines connected to the hand-held device. This applies, in particular, to the avoidance of a connecting line to an external vacuum source and/or power supply. Moreover, the pressure source with which the generation of a vacuum is preferably to be achieved should be designed to be as simple as possible and should operate reliably. If possible, the removal of tissue samples should occur in such a way that the user, in most cases a pathologist, can be provided with a non-drilled and undamaged tissue sample for evaluation. Finally, the biopsy device should be inexpensive and should allow for a cost-efficient solution with respect to replaceable biopsy needles, which are to be viewed as disposable material.

The solution of the objective underlying the invention is a biopsy device designed in accordance with the present invention, which may comprise a biopsy needle module that can be implemented in the inventive biopsy device for its functional application. In addition, a method of removing tissue using the inventive biopsy device is disclosed. Advantageous embodiments of the inventive concept can be derived from the description, especially with reference to the exemplary embodiments.

The inventive biopsy device for tissue removal in the form of a manual component with at least one elastic force-actuated clamping and shooting device in the form of a clamping cradle for a biopsy needle unit, which features an outer hollow needle with a distally sharpened cutting blade and a hollow biopsy needle mounted in the interior of the hollow needle with a tissue sample removal chamber provided in its distal end region, wherein the outer hollow needle is slidably seated relative to the hollow biopsy needle, as well as with a pressure source connectable to the hollow biopsy needle, is characterized, according to the invention, by the fact that the hand-held unit 1 features a housing in which at least two drive elements as well as the clamping and shooting device in the form of a clamping cradle are securely and detachably integrated. The two drive elements and the clamping cradle are designed and disposed inside the housing in such a way that the biopsy needle unit seated in a biopsy needle carrier and a pressure source connected to the biopsy needle unit can be implemented in the interior of the housing, and can actively engage the components disposed therein and mentioned above in a suitable manner. The biopsy needle unit, with its hollow biopsy needle, is connected in a gas-tight manner to the pressure source via a connecting line and represents a self-contained biopsy needle module which, for reasons of sterility, must be viewed as a disposable article.

On the one hand, the biopsy needle carrier serves as a mechanical receptacle structure for the biopsy needles, of which at least the outer hollow needle, which will be described in detail below, is moveable, by means of a spindle mechanism, by rotation around the longitudinal axis of the needle and along the hollow biopsy needle. On the other hand, the biopsy needles are jointly detachably connected to the clamping cradle through the biopsy needle carrier, through which the process of shooting both biopsy needles into a tissue region to be examined is performed. To this end, the biopsy needle carrier features a suitable coupling structure, which can be inserted into a corresponding counter-coupling structure on the clamping cradle.

In a preferred embodiment, the biopsy needle carrier features a housing module, open at one end, through the open end of which the biopsy needles can be securely but detachably integrated into the biopsy needle carrier. In addition, the design of the biopsy needle carrier, with its open end being open, permits a drive element attached to the outer circumference of the outer hollow needle to mechanically engage a gear component, which is attached to the drive shaft of one of the drive units. As a result of this kinematic active connection existing between the outer hollow needle and the drive unit, the outer hollow needle can brought into rotation, which results in said outer hollow needle being shifted relative to the needle longitudinal axis of the hollow biopsy needle, which is firmly attached in the needle longitudinal direction of the biopsy needle carrier. It is precisely this kinematic mode of action that also triggers the clamping of the clamping cradle, in that, once a mechanical limit stop is reached on the outer hollow needle, which is longitudinally moveable relative to the hollow biopsy needle, the biopsy needle carrier and the biopsy needle arrangement are shifted in the clamping direction, together with the clamping cradle, until the clamped position is attained.

As a result, two functions can be served using only one driving mechanism, i.e., clamping the clamping cradle and triggering the motion of the biopsy needles, which is not limited to the relative longitudinal displacement of both biopsy needles, but rather, as will be demonstrated below, optionally includes additional rotational movements around the needle's longitudinal axis. In addition to the drive unit mentioned above, the sole function of the second drive unit is the targeted generation of a pressure level within the hollow biopsy needle and the tissue sample removal chamber connected to it. Depending on the respective procedure being performed with the biopsy device, the pressure level represents either an overpressure or a vacuum, which can be generated and adjusted in a targeted manner using the pressure source.

Using the biopsy device designed in accordance with the invention, it is possible to perform a fully autonomous tissue sample removal process which, moreover, can be performed by a physician in connection with single-handed operation. All procedures needed to remove a tissue sample take place automatically, i.e., without additional manual support, and can each be triggered by individual keystroke verifications on the biopsy device itself.

The individual steps required for complete tissue removal are accomplished by the biopsy device in the following manner: 1) placement of the biopsy needle unit and the clamping cradle into a starting position (this first step is a form of reset function); 2) placement of the clamping cradle into a tensioned state; 3) triggering of a shot, by means of which the biopsy needle unit is distally shot into a tissue region to be examined; 4) automatic development of a vacuum, which can be applied by the pressure source, through the connecting line, along the hollow biopsy needle, and into the tissue removal chamber; 5) tissue severing process, in which the outer hollow needle is shifted proximally and, at the same time, the tissue removal chamber is released under vacuum conditions, which results in surrounding tissue material being sucked into the tissue removal chamber and being severed from the remaining tissue by the cutting action along the longitudinal edges laterally bordering the tissue removal chamber and configured as cutting edges, wherein the severing process is additionally supported by a periodic distally and proximally directed change in motion of the hollow biopsy cannula, so that, finally, the partially severed tissue sample, which has been sucked into the tissue sample removal chamber, is completely severed by the outer hollow needle being pushed distally forward; and 6) tissue sample removal process, which takes place outside the body, and in which the outer hollow needle proximally releases the tissue sample removal chamber, at least in part, and, due to application of overpressure through the hollow biopsy needle, especially in the lower region of the tissue sample removal chamber, severing of the tissue sample is brought about, as a result of which the tissue sample is easily removable from the tissue sample removal chamber.

The procedures described above for careful tissue sample removal can be reliably and safely performed using the biopsy device of the invention. Of particular significance is the fact that the biopsy device is completely independent of external devices supporting the tissue removal process, while at the same providing a high degree of ease of operation, thus easily allowing for single-handed operation. The biopsy device will now be explained in detail while making reference to the exemplary embodiments described below.

The biopsy device is especially advantageously characterized by the instrument panel to be operated by a treating physician, which is provided in an exterior side wall of the housing of the biopsy device and preferably features only three control keypads, which are installed in an especially clear manner and can be operated completely without error. Thus, for example, light signal fields are assigned to each control keypad, which provide the physician with information on the current operability of the individual control keypads and, furthermore, ensure a predetermined completion of functions in accordance with the process described above. Functions that are to be performed with special care, such as the clamping of the clamping cradle or the operation of the tissue sample removal process, are equipped with a time delay feature, so that they cannot be triggered inadvertently. The biopsy device is advantageously characterized by these and many other special features, as can be deduced from the following discussion, in which reference is made to the following exemplary embodiments.

BRIEF DESCRIPTION OF THE DRAWINGS

In the following, the invention is described in exemplary fashion, but without limiting the general concept of the invention, on the basis of exemplary embodiments and while making reference to the drawings.

FIG. 3 depicts a longitudinal section A-A through the biopsy needle shown in FIG. 1.

FIG. 3a depicts a longitudinal section A-A through the biopsy needle shown in FIG. 1 (as in FIG. 3), proximal portion (enlarged).

FIG. 3b depicts an enlargement of segment A in FIG. 3a.

FIG. 3c depicts an enlargement of segment B in FIG. 3a.

FIG. 4 depicts a cross-section B-B in FIG. 3 (left section of housing).

FIG. 5 depicts a cross-section C-C in FIG. 3 (right section of housing).

FIG. 6 depicts the right housing end lid (interior) with integrated microswitch.

FIG. 8a depicts the base block in the x-axis, viewed from the front (perspective view).

FIG. 8b depicts the base block in the x-axis, viewed from behind (perspective view).

FIG. 9a depicts the hand-held unit with the units of the biopsy device attached to the housing, without the housing lid and base and in the non-tensioned state.

FIG. 10a depicts the depiction of FIG. 9, but with the clamping cradle in its tensioned position.

FIG. 10b depicts the depiction of FIG. 9a, but in the tensioned position and in the locked position.

FIG. 11a depicts the biopsy needle tip in a side view.

FIG. 11b depicts a longitudinal section through FIG. 11a (sample removal chamber opened).

FIG. 11c depicts the depiction of FIG. 11b, but with (sample removal chamber half-opened).

FIG. 11d depicts the depiction of FIG. 11b (sample removal chamber closed by means of cutting sleeve.

FIG. 11e depicts section A-A in FIG. 11a.

FIG. 11f depicts section B-B in FIG. 11a.

FIG. 11g depicts an enlargement of the cut edge at A.

FIG. 12a depicts a section through the longitudinal axis of the proximal portion of the biopsy needle (enlarged).

FIG. 12b depicts section B-B through the multiple edge of the biopsy carrier in the rotated state; left limit stop.

FIG. 12c depicts section B-B as depicted in FIG. 12b, but with multiple edge in its centered position.

FIG. 12d depicts section B-B as depicted in FIG. 12b, but pivoted; right limit stop.

FIG. 12e depicts section A-A through needle deformation zone 0 of the biopsy needle and the cutting sleeve.

DETAILED DESCRIPTION OF THE INVENTION

The following detailed description should be read with reference to the drawings, in which like elements in different drawings are identically numbered. The drawings, which are not necessarily to scale, depict selected preferred embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Figure 1:
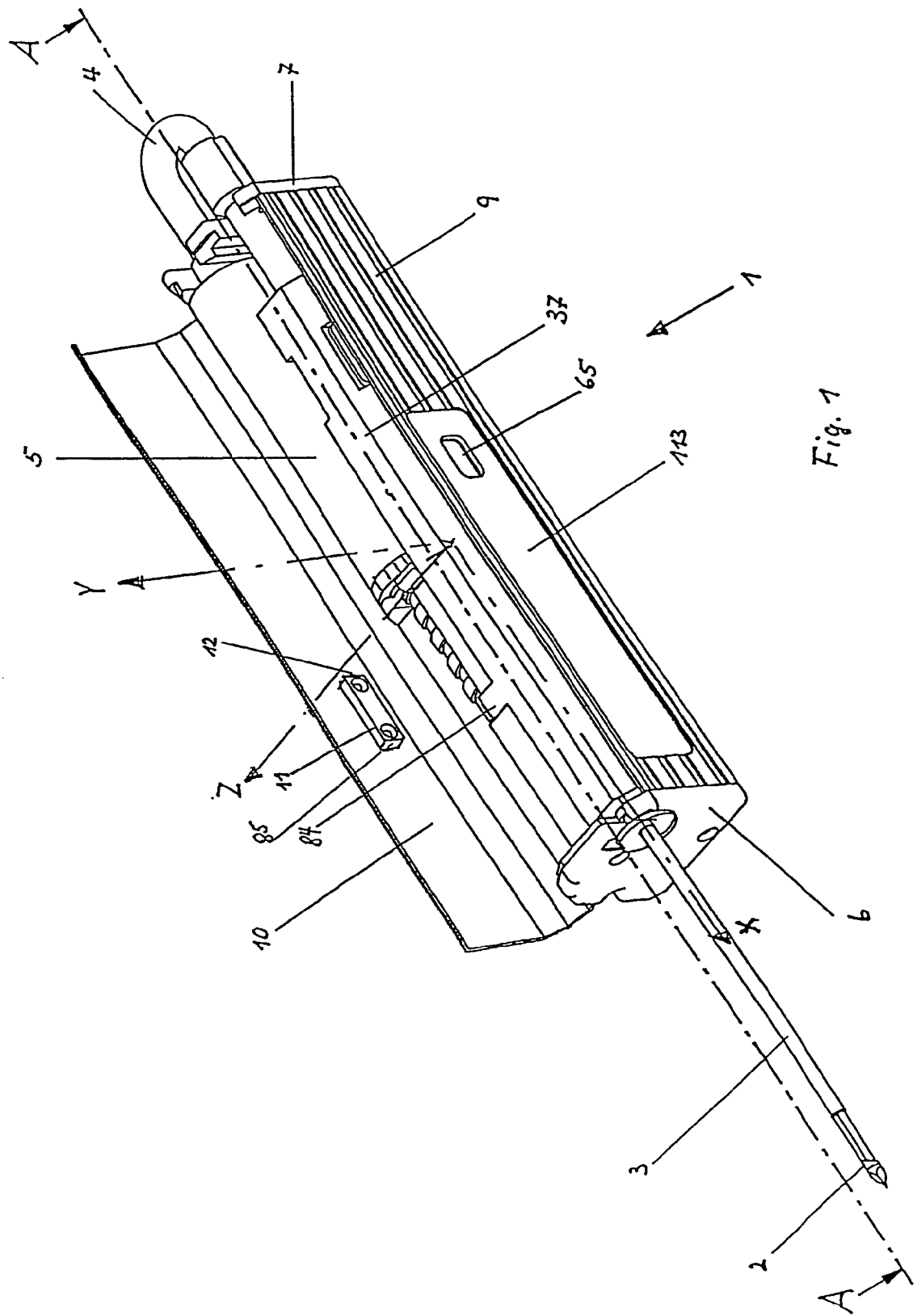
FIG. 1 depicts a biopsy device with an opened housing lid (perspective view).

In the exemplary embodiment depicted in FIG. 1, all components necessary for the completion of a vacuum biopsy are integrated into the interior space of the housing of a hand-held unit 1, so that no cables or lines from the housing of the hand-held device to other external supply units are necessary. The hand-held unit 1 thus represents a complete vacuum biopsy device, which is freely moveable in all directions.

The distal portion of the hollow biopsy needle 2 and the outer hollow needle 3, which surrounds it coaxially and is referred to in the following as the cutting sleeve, protrude from the distal housing lid 6. Said cutting sleeve is used to remove and/or completely sever the tissue sample. In most instances, a coaxial cannula, which is not depicted, is inserted into the tissue, into which this segment of the biopsy needle 2 with cutting sleeve 3 is introduced and is thus positioned in front of the tissue to be examined. A connecting element 4, such as a transparent, flexible tube, which connects the pressure source disposed in parallel to the biopsy needle or the vacuum pressure-generating device 5 with the internal hollow space of the biopsy needle 2 in a gas-tight manner, is disposed outside the right proximal housing lid 7. The hollow connecting element 4 lies in direct proximity to the housing lid 7.

Figure 2:
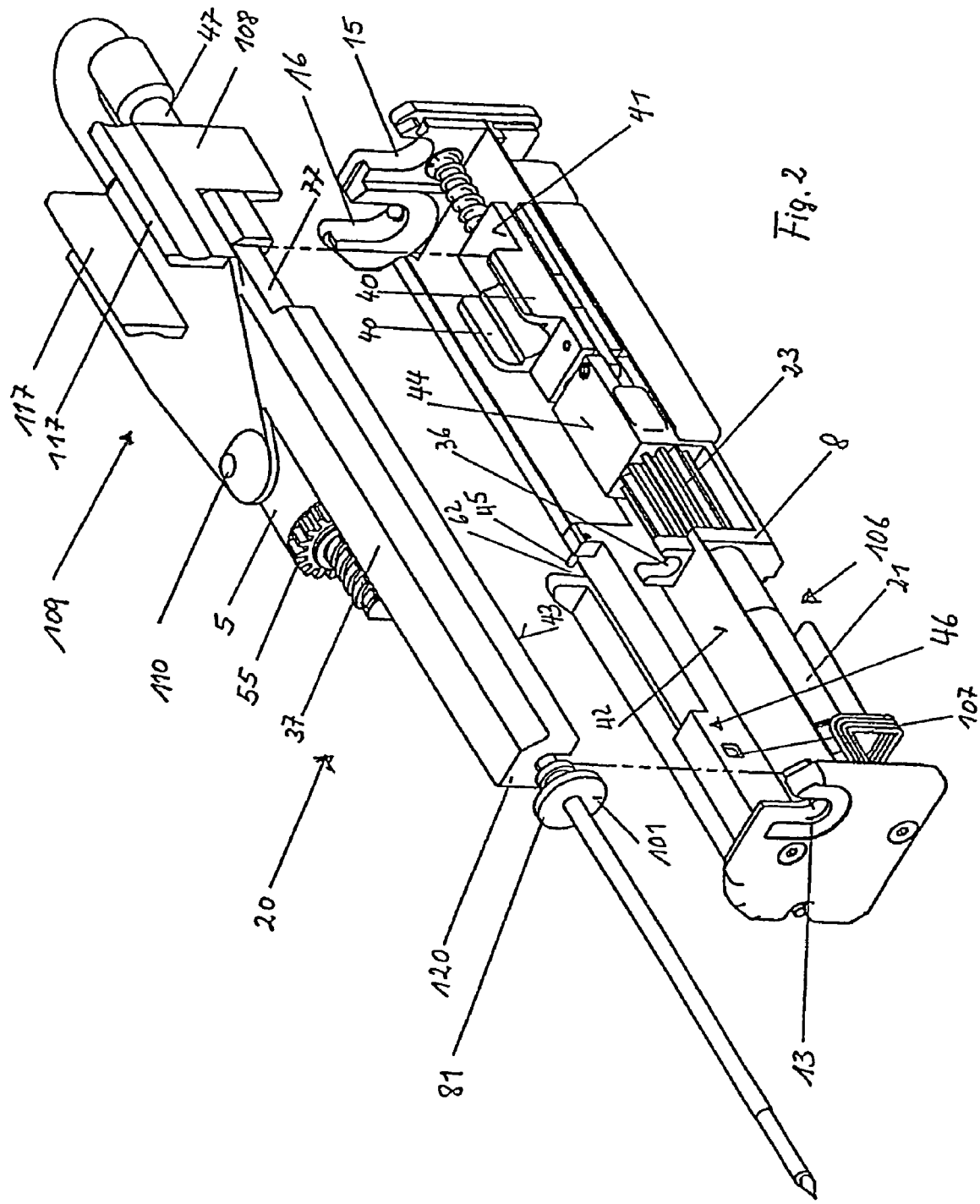
FIG. 2 depicts a hand-held device with parts of the biopsy device arranged therein (without housing base and lid) and interchangeable biopsy unit (highlighted in a perspective view).

The biopsy needle 2 with cutting sleeve 3 and additional elements, disposed in a biopsy needle carrier 37, forms, together with the connecting element 4 and the vacuum pressure-generating device 5, a biopsy needle module 20 that is easily removed in an upward direction and easily inserted, hereinafter referred to as the removable element, which can be replaced as needed (FIG. 2). The housing lid 10 is opened for this purpose. As FIG. 2, in particular, shows, the biopsy device can be divided into parts that are firmly attached to the housing (disinfected parts) and a removable element 20 (sterile part). While the parts that are firmly attached to the housing are only disinfected, the removable element 20 is delivered in sterile packaging and is replaced as necessary, particularly with each new patient. As will be explained in detail later on, steps have been taken to ensure that the disinfected part is not contaminated with tissue fluid during use.

In the exemplary embodiment described below, the vacuum pressure-generating device 5 is arranged in parallel to the biopsy needle unit. Within the scope of the invention, however, the vacuum pressure-generating device 5 can also be arranged in a prone position in the axle of the biopsy needle or the hand-held unit 1. Furthermore, it does not require a separate connecting element if, for example, it is placed directly onto the end of the biopsy needle. In this case, the connecting element is to be viewed as a suitable flange connection, such as in the form of a Luer lock.

A lower housing segment 9 and a housing lid 10 hinged in the housing end lids, together with a locking latch 11, are positioned between the left and right housing end lids 6, 7. The lower housing segment 9 is clamped between the housing end lids 6, 7 and/or connected to a base block 8 by means of tension rods or screws, some of which are screwed into the base block 8. The housing lid 10 is hinged to an axle secured in the housing end lids 6, 7. The housing lid 10 is closed prior to operation of the biopsy device, with the inside contour of the housing lid corresponding to the outside contour of the biopsy needle carrier 37, which will be described in detail later on. The base block 8, which is firmly connected to the lower housing segment by means, for example, of fixing elements and/or a screw connection, is disposed at approximately the center of the interior space of the housing. The drive elements for the vacuum pressure-generating device 5, the cutting sleeve 3, and the clamping device for the clamping cradle 28, onto which the biopsy needle carrier 37 is mounted, are connected to the base block 8. The base block 8 extends from the center of the housing to the left, and a plate joined to it cover the drives and serves as a support for the control board, which is arranged a protected manner inside or below the cover 46. In addition, the base block 8 features a holder 36, open at the top, for both the biopsy needle and cutting sleeve, as well as an additional insertion element 62 for the vacuum pressure-generating device 5.

To identify the position of the individual elements, as well as the position of the individual parts, especially in the interior space of the housing, a system of coordinates was drawn in FIG. 1, wherein the center point of the coordinates of the system lies at the center of the base block 8 (FIG. 1). Accordingly, in the following description movement in the direction of the x-axis is considered left (distal) and movement away from the x-axis is considered right (proximal). For the remaining coordinates, movement in the direction of the y axis is considered upward, movement away from the y axis downward, movement in the direction of the z axis backward, and movement away from the z axis forward (FIG. 1). Therefore, the system of coordinates divides the interior space of the housing and the remaining references into left and right, front and back, and top and bottom. To facilitate understanding, these rules were modified for depicting angled rotational movement of the biopsy needle, with rotation around the common longitudinal axis of the biopsy needle and the cutting sleeve being depicted as movement to the left (i.e., toward the front) and right (toward the back).

With reference to these rules, the common drive mechanisms 106 for the clamping device and the cutting sleeve are located in approximately the lower, front, left portion of the interior space of the housing, and the drive mechanism for the vacuum pressure-generating device 5 in the upper, rear, left portion of the housing. The power supply for the drive motors and the remaining electronic components, such as the control and/or monitoring elements, are located in the lower, right portion; batteries or a storage battery 111, such as a 7.2 V lithium ion battery, 1 Ah, are preferably used for this purpose. The front, right, upper interior space of the housing located above the battery space is used primarily for the clamping cradle 28 and locking element (FIG. 5), which is connected to a block 26, which is part of the base block 8. The battery space is sealed at the top by a divider plate 114.

In the uppermost, front portion of the interior space of the housing, an insertable and removable biopsy needle carrier 37 is arranged in the U-shaped insertion holder 36, open to the top, of the base block 8 and in the upward-pointing bracket 40 disposed on both sides of the clamping cradle 28, a biopsy needle/cutting sleeve unit with drive components being rotatably supported in said biopsy needle carrier, which extends along virtually the entire length of the hand-held unit 1. As described later on, the biopsy needle carrier is longitudinally displaceable by means of the clamping cradle. This means that in the non-tensioned state the left face of the biopsy needle carrier 37 almost rests against the housing end lid 6 and, in the tensioned state, the right face rests against the right housing end lid 7. "Virtually the entire length" signifies that the biopsy needle carrier is shortened by at least the amount of interior housing space required for the clamping process. If the clamping path of the clamping cradle is, for example, 20 mm, the biopsy needle carrier must be displaceable by at least this amount. In general, the clamping path ranges from 15 to 25 mm, depending on the biopsy needle used. Consequently, it is advantageous to design the interior space to include the largest possible clamping path, plus a few mm.

The clamping device (right, at front) itself comprises a clamping cradle 28 traveling on a pin 30, the pin being screwed into the block 26 of the base block 8. The pin 30 is proximally encircled by a spiral spring 31. Another short spiral spring 124 is disposed on the pin 30 on the distal side of the clamping cradle. One side of this short spiral spring rests on the block 26, while the other side rests on an inner lip 122 on the distal side of the clamping cradle. The spiral spring 31 rests on the opposite side (proximal side) of the lip of the clamping cradle. The locking mechanism (see, in particular, FIGS. 9b and 10b) of the clamping cradle is secured to the block 26. The vacuum pressure-generating device 5 and parts of the drive are arranged in the upper, rear, right interior space of the housing; the drive motor for the reduction gear for the vacuum pressure-generating device 5 is located in the left, lower, rear region of the interior space of the housing. The housing lid, the lower housing segment, the housing end lid and the base block are preferably made of aluminum.

As described earlier, the hand-held unit 1 comprises a housing, which consists of a lower housing segment 9 with lateral walls of different heights, a housing lid 10, matched to the lower housing segment, with longitudinally displaceable locking mechanism 11, and the two housing end lids 6, 7. The lower housing segment is connected to the two housing end lids by means of tension rods or screws made, for example, of iron, some of which are screwed directly into the base block 8. The housing is approximately 200 mm in length, the housing end lids feature a section cross-section of approximately 40×40 mm (FIG. 2). The housing lid 10 pivots around an axle 104 secured in the housing end lids 6, 7; the holes in the housing end lids are used for this purpose. The nose 12 of the locking mechanism 11 can be inserted into the depression 45 in the base block 8 to lock the housing lid. The left housing end lid 6 features, in its upper front portion, a U-shaped opening 13, which is open at the top, for the forward-protruding portion of the biopsy needle/cutting sleeve 2, 3 and the guide roller 81 disposed thereon. The guide roller 81, which is placed onto a coaxial cannula when said cannula is used, also prevents tissue fluid from penetrating into the housing. The rear housing end lid 7 features two U-shaped openings 15, 16, which are open at the top. The opening 15 corresponds to the passageway 13; it accepts the end of the round-profile plastic component 47 placed onto the hollow biopsy needle. A nozzle 63 of the vacuum pressure-generating device 5 is placed into the opening 16 (FIG. 2).

Another plastic component 112 inserted into the plastic part 47 features a peg 17, which is used to connect the connecting element 4 with the outflow nozzle 64 of the vacuum pressure-generating device 5. The interior hollow space of the biopsy needle is continuously connected with the hollow space of the piston/cylinder arrangement and the hollow space of the vacuum pressure-generating device 5 by means of the connecting element 4, which is also hollow. The connections are designed in such a way that air cannot penetrate into the system from the outside, nor can air escape to the outside when there is overpressure; in other words, the points of connection are designed to be airtight. The system, designed in this manner, causes the sealing element 76 to be pulled against the biopsy needle 2 when a vacuum is applied to the interior of the biopsy needle, which substantially improves sealing action, but does not negatively affect the rotational movement of the cutting sleeve relative to the biopsy needle, but, if suitably designed, does rotate the biopsy needle until the rotation is stopped by a limiting device.

As FIG. 6, in particular, shows, a microswitch 18 is integrated into the lower end of the hole 16 in the housing end lid 7, and its switching pin 19 protrudes into the hole. As soon as the nozzle 63 of the vacuum pressure-generating device 5 is inserted into the hole and the housing lid is closed, the switching pin 19 of the microswitch 18 is pressed downward and the microswitch 18 releases the current supply. The terminals for connecting a charging device can be installed into the holes 97, 98 in the housing end lid.

Figure 7:
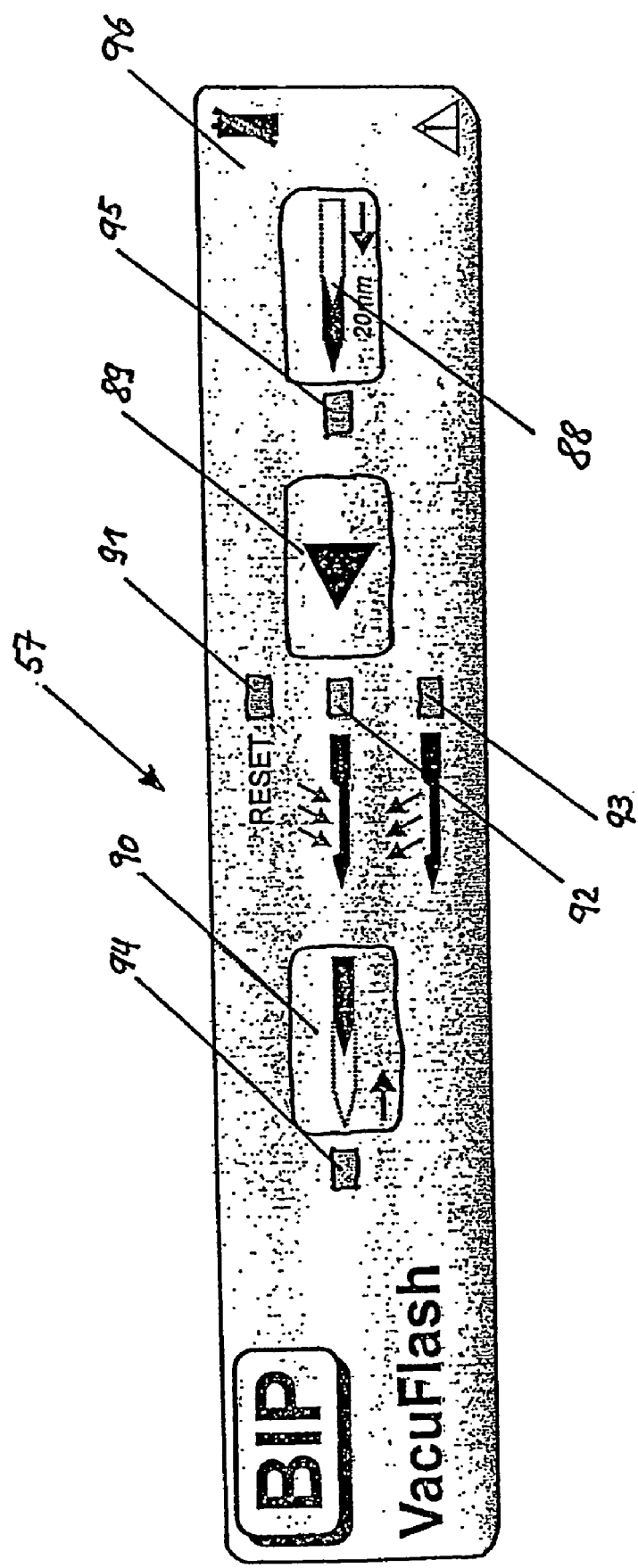
FIG. 7 depicts the front side of the control panel.

A surface 113 for the control panel (FIG. 7) with control and monitoring elements is provided on the front side of the lower housing segment 9. The control panel 57 to be attached to the housing is designed as an independent component which, for example, is glued to the surface 113 of the lower housing segment 9. This control panel 57 is connected to other electronic components disposed in the housing, as well as with the power supply, by means of cables. Of the electric/electronic components connected to the control panel, the circuit board disposed in the space 139 located (see FIG. 4) beneath the cover 46 is especially worth mentioning. A programmable microprocessor, as well as other electronic components, is disposed on the circuit board. The microprocessor is used to control the semi-automatic process control described later on. The control panel contains, in particular, switches to operate the biopsy device and diode to control the operating process. The control key 88 for mechanically triggering the clamped clamping cradle protrudes from a depression 65 in the lower housing segment and somewhat presses out the control panel disposed above it, so that the control key can easily be felt through the foil of the control panel.

In designing the control and monitoring elements, steps were taken to ensure that a distinction is drawn between the clamping process of the clamping cradle and the triggering of the clamping cradle, on the one hand, and, on the other hand, between said clamping process and performance of the biopsy, such as severing of the sample and, in particular, sample removal by means of ejection of the sample. Accordingly, the control key 88 (actuator) for the clamping cradle was placed to the right, while the clamping key 90 that triggers clamping of the clamping cradle was placed to the left. The program key 89 for completing the biopsy is centered. The control lights for reset, completion of the biopsy and ejection of the sample when the sample removal chamber is opened are also centered. When the program key 89 is pressed following insertion of the removable element 20 and following closing and locking of the housing lid, as well as automatic setting of the basic position, two functions are activated, namely sample removal and sample ejection.

Following insertion of the removable elements and closing of the lid, the yellow reset diode 91 is briefly illuminated and then flashes during setting of the basic position; the reset diode is extinguished following setting of the basic position. The sample removal diode 92 (green) and the clamping diode (yellow) are illuminated and indicate that the operator can activate one of the two functions. If he presses the clamping key 90, the clamping cradle 28 is brought into clamping position and locked in this position. To prevent the clamping key from being pressed inadvertently, it is equipped with a delay circuit of about 1.2 seconds. The yellow clamping diode blinks during the clamping process. Following completion of the clamping process, the locking diode (green) blinks. The device, i.e., the biopsy needle, is then ready to be shot into the tissue to be examined and is triggered by means of the control key 88. Following the shot into the tissue, the locking diode is extinguished and the clamping diode (yellow) and the sample removal diode (green) are illuminated. Both functions (clamping or sample removal) can now be activated.

When the program key 89 is pressed, the biopsy process is performed automatically, as explained later on. However, the clamping process could also be activated again. When the biopsy process (sample removal) is activated, it takes place automatically. Following completion of the process, the flashing green sample removal diode is extinguished and the yellow ejection diode is illuminated. When the program key is pressed again, the automated sample removal process is performed. Following completion of the process, the flashing ejection diode is extinguished and the yellow reset diode is illuminated, which means that the removable element 20 can be removed, or that it can be automatically prepared for removing an additional sale by pressing the program key. This is followed by process as described above, i.e., either clamping or sample removal. For the event that the program key 89 is pressed for sample removal (to eject the sample), a delay circuit is provided that prevents ejection from occurring if the program key is touched inadvertently before the needle has been removed.

The battery charge diode 96 indicates the charging condition of the battery or storage battery. As described earlier, the diodes are wired in such a way that the diode flashes during completion of the specific process that was activated, and that the diode for the ensuing process is illuminated following completion of the process. If two options are available, both subsequent diodes are illuminated. In this case, the operator may select the option of his choice. The colors of the diodes are selected in such a way that procedures in the tissue are indicated by a green light, while external procedures are indicated by a yellow light. Delay circuits (e.g., 1.2-1.5 seconds) are provided for the functions or clamping and sample removal, so as to ensure that the process is activated deliberately. The mode of action and control options are discussed in greater detail during the description of the process sequence. Symbols (pictograms) on the board symbolize the individual processes.

A perspective view of the base block 8 (as seen from the front in the direction of the x axis) is shown in FIG. 8a, while FIG. 8b depicts the base block 8 from behind in the x-axis (both are perspective views). The base block 8, when viewed in a longitudinal direction, can be divided into two halves; the front section is used to secure the common drive for the cutting sleeve and the clamping cradle and, in its front portion, to support the biopsy needle carrier (FIG. 8a); the rear section is used to secure the drive for the vacuum pressure-generating device 5 as well as the support for the distal side of the vacuum pressure-generating device 5 (FIG. 8b). A central electronics circuit board is disposed between the two drive motors 21, 58, below the center rib 87, in the space 139 beneath (see FIG. 4). The base block 8 features, in its left, front portion, a U-shaped space 24, in which a toothed roller 23 driven by the geared motor 21 is installed. To this end, the drive shaft of the geared motor is supported and/or inserted in an opening in the wall 25 of the base block 8. The toothed roller 23 is mounted onto the drive shaft and is attached to it and secured against rotation and displacement by means of a screw. On the other side, the toothed roller 23 is supported in the wall 22 of the base block 8. A DC motor with a rotation speed of approximately 11000 RPM is used as the drive motor. A planetary gear with high gear reduction is installed downstream from the DC motor, with the toothed roller 23 mounted on its drive shaft.

Molded to the wall 22 and pointing to the right is another block 26, which both accepts the pivoting double-armed handle 33 for the locking mechanism and serves to secure the pin 30 guiding the clamping cradle 28. The pins 30 are screwed into the threaded bore 29. During the clamping process, the clamping cradle 28 slides to the right on the divider plate 114 disposed below it. During the clamping process, the spiral spring 31 disposed on the threaded pin 30 is compressed. One end of the spiral spring rests against an end piece 32 of the threaded pin or directly on the housing end lid 7; the other end of the spiral spring, which protrudes into a blind hole in the clamping cradle, rests against ship resting on a lip 122 of the guide hole 115. The threaded pin 30, secured to the housing end lid 7 at one end and to the block 26 at the other, carries at its distal end a short spiral spring 124, which also rests, on its proximal side, against another shim 125 resting against the circumferential lip 122 in a coaxial blind hole 129 opposite the hole 115. Both spiral springs have the same diameters, and the diameters of the distal and proximal bore 129, 115 in the clamping cradle and the distal bore 128 in the block 26 are such that the spiral springs can be easily inserted. All bores are coaxial to the pin 30. The threaded pin 30 features a band 123 at the same axial distance to the circumferential lip in the blind hole of the cradle. In its starting position (resting position), the clamping cradle 28 is held in resting position by slightly loaded springs 31, 124 over the shims, as depicted in FIGS. 3a and 3c.

The shims rest against both the corresponding side of the band and the lip, and are vertically disposed. Thus, if the cradle is deflected to the right or left, the respective spring will attempt to return the clamping cradle to its starting position; in a manner of speaking, the clamping cradle is "swimming." The clamping cradle 28 slides on the divider plate 114, in particular, and is prevented from rotating by said cradle and by the side wall. An arm 99 of the double-armed handle 33 of the locking device engages a groove 27 of the clamping cradle 28 (FIGS. 9a and 10a). The locking device integrated into the block 26 of the base block 8 consists of a double-armed handle 33, which pivots around a vertical axis (seen in the y axis) by means of a compression spring 34. The axis 35, a vertically disposed pin, is secured in the bores 38 of the base block. In the resting state, the part 99 of the double-armed handle lies in the groove 27 of the clamping cradle; the compressed spring 34 acts on the part 100 of the handle and presses the locking key 88 outward (toward the front). The locking key is easily felt in the control panel, which is pushed slightly outward at this point after clamping.

As soon as the part 99 of the double-armed handle can lock into the depression 82 in the clamping cradle, the control key 88 is pushed outward. As a result of the locking of the handle part 99, the clamping cradle is locked in its the clamping state and can be triggered, if needed, by pressing the control key 88. As the clamping cradle is advantageously made of plastic, it has proven to be advantageous to place a metal part 83 into the depression so as not to damage the plastic, as the double-armed handle is also made of metal. In contrast to the removable element 20, the hand-held unit 1 with replaceable insert is reused several times. The clamping path corresponds to the depth of penetration of the biopsy needle into the tissue. Consequently, the length of the handle 99 also corresponds to the clamping path. As the depth of penetration generally ranges between 15 and 25 mm, the same hand-held unit 1 can be used for various depths of penetration by suitably designing the handle 99 and modifying the settings in the control unit accordingly.

The clamping cradle 28, which is adjacent to the block 26, is disposed at the same height as the block 26, and has approximately the same profile as the block 26. The clamping cradle features two brackets 40 on its upper side. The upward-facing surface 41 of the clamping cradle, the upward-facing surface 44 of the block 26, and the upward-facing surface of the extension 42 of the base block 8 together form a flat support surface for the lower sliding surface 43 of the biopsy needle carrier 37 to be mounted (see FIG. 2). The biopsy needle carrier is made of plastic. When the clamping cradle is shifted from its non-tensioned resting state (FIG. 9a) to its clamped state (FIG. 10a), i.e., to the right, the biopsy needle carrier 37 held by the brackets 40 slides across the surface 42 and 44. It is also conceivable that the sliding surfaces are not flat, as in the exemplary embodiment, but feature uniquely structured sliding surfaces; what is important is that the biopsy needle carrier 37 can slide easily and in a straight line on the sliding surface, and that, once the control key 88 has been triggered, the biopsy needle can penetrate into the tissue, the tumor, in a straight line. For this reason, the upper outside contour of the biopsy needle carrier is also shaped to conform to the inside contour of the housing lid and features only a small amount of play to the housing lid, so as to prevent upward deflection of the biopsy needle, which is also advantageous during the clamping process.

Above the U-shaped space 24 for the toothed roller 23, at the level of the sliding surface 42, the base block 8 has a U-shaped holding device 36, which is open to the top, for inserting the biopsy needle/blade sheath, among other things. The primary function of this holding device is that of a radial thrust bearing, i.e., it supports the drive part that is connected to the blade sheath, namely the gear 74 or the plastic disk 78, in order to bring the clamping carriage into its clamped position by means of the drive device 106. On the distal side, the holding device also serves as a stop for the collar 127 in the execution of the back-and-forth movement and the associated angular-rotation movement.

A further U-shaped insertion element 62 is provided in the rear, upper part of the base block; the free end 61 (distal end) of the threaded spindle of the vacuum- and pressure-generating device 5, the end protruding from the syringe body, is inserted into the insertion element. The insertion element is embodied as a conduit, in which the threaded spindle 53 slides. In the upper, central region of the base block, a fastening device is provided for a disk that is received by the recess 45; the latch 12 of the locking bar 11 of the housing lid is pushed into the fastening device. A cover 46, which is disposed on the base block 8 and faces left, separates the space for the drive motors and the inserted plate from the upper, left portion of the housing interior, which primarily serves in seating the replaceable biopsy-needle carrier 37, including the biopsy needle and the blade sheath. The cover 46 protects the electrical gear motors and the plate from contamination. The plate for the electronic components lies between the drive motors, and beneath the center rib in the space 139 (see FIG. 4). FIG. 2 illustrates the biopsy-needle carrier 37, which can be inserted into the brackets 40 of the clamping carriage 28 with the biopsy needle 2 and the blade sheath 3, as well as further parts.

The hollow, circular biopsy needle 2 has a needle tip 70, which the specimen-collection chamber 71 adjoins (FIGS. 11a-11f). The biopsy needle 2 having a round cross-section is surrounded coaxially by a blade sheath 3, also having a round cross-section, and having at its left end, which faces the specimen-collection chamber 71, a blade 72. In an especially preferred embodiment, after the biopsy needle has been inserted (with the specimen-collection chamber 71 being closed) and the specimen-collection chamber 71 has been opened, and the needle has performed a repeated back-and-forth movement that is superimposed simultaneously by a predetermined, limited angular-rotational movement of the biopsy needle about its longitudinal axis, the blade serves in cutting out the specimen and holding it in the closed specimen-collection chamber 71, as will be explained in detail below. The distal blade of the blade sheath is preferably disposed perpendicular to the longitudinal axis of the biopsy needle and the blade sheath.

Figure 11:
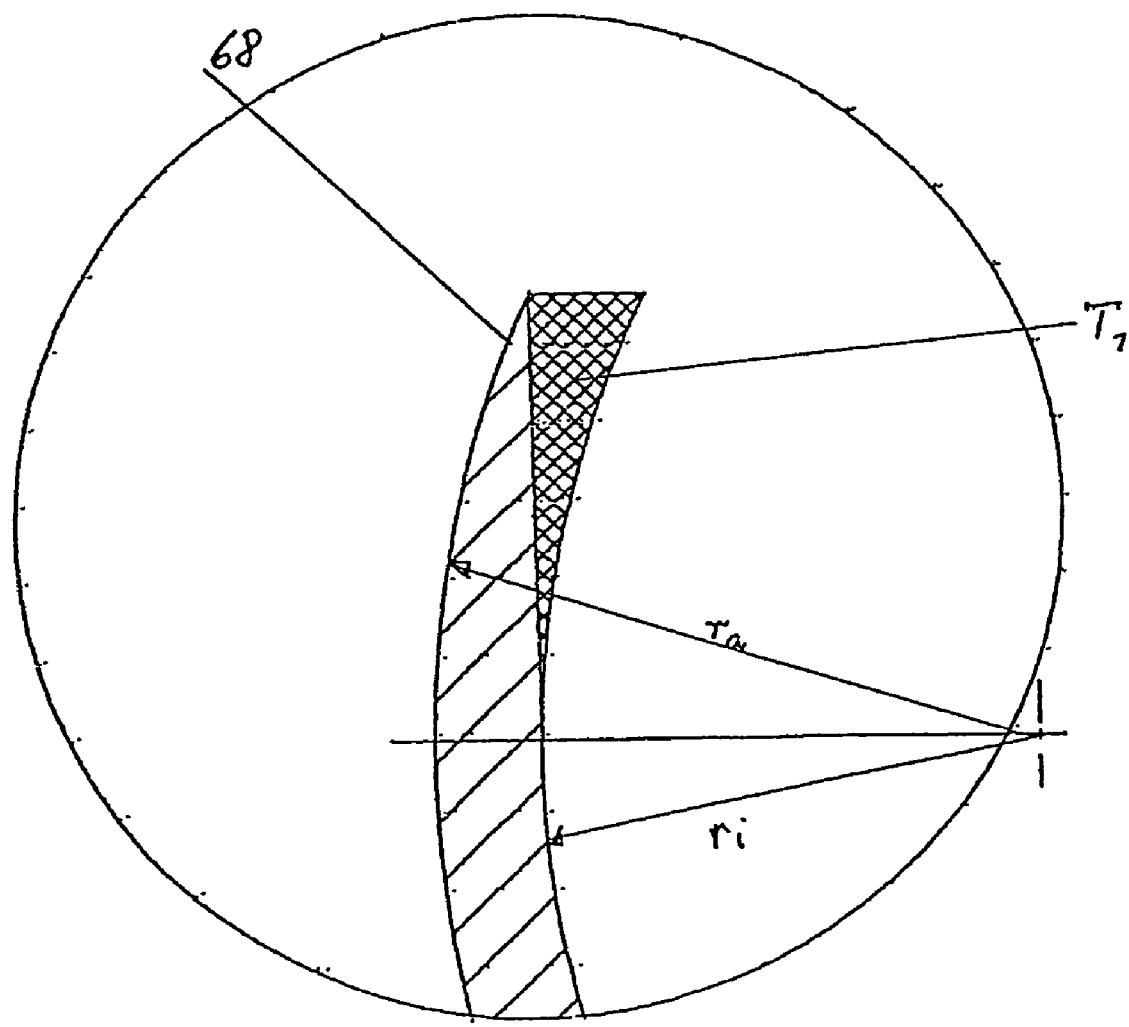

The severing procedure is preferably effected through the rotation and simultaneous longitudinal displacement of the blade sheath by the threaded-spindle drive. It is also conceivable for the blade sheath not to execute a continuous movement, but for it to move in increments or to vibrate, i.e., the traveling part is moved forward and back by short distances. As can especially be seen from the cross-sectional representation in FIG. 11f, the longitudinal edges 68 of the specimen-collection chamber 71 are located above the center point of the cross-section—in other words, the specimen-collection chamber 71 extends beyond the Z-axis by about 15-30°. To improve the entrance of solid, hard tissue into the specimen-collection chamber 71, the longitudinal edges have a blade. This blade at the longitudinal edges is created through the reduction of the wall thickness from above such that the width b' at the cutting edge corresponds to the width b of the diameter of a lower-lying blade-sheath-tube, i.e., the wall thickness is reduced in the upper part and utilized to embody the cutting edge (FIG. 11f and enlarged view in FIG. 11g).

At the other, proximal end of the blade sheath, which faces away from the blade 72, a threaded-spindle sheath 73 is secured to a gear 74 that is disposed at the end face of the threaded-spindle sheath. The threaded-spindle sheath is disposed with the gear on the blade sheath so as to be fixed against rotation and displacement. A threaded-spindle nut 75 that is pressed securely into the biopsy-needle carrier 37 cooperates with the threaded spindle. The gear 74 is to the left, that is, in front of the beginning of the spindle sheath. When the threaded-spindle sheath is rotated by the gear 74, the blade sheath is rotated and displaced longitudinally over the biopsy needle 2.

On the distal side of the gear 74, a tubular piece 126 having the collar 127 is permanently connected to the threaded spindle. The tubular piece is inserted into the holding device 36, with the collar 127 being located on the distal side in front of the holding device. The length of the tubular piece 126 approximately corresponds to the clamping path; the wall thickness of the holding device 36 must additionally be considered here (FIGS. 3a and 3b). In the initial position of the device (closed specimen-collection chamber 71), the collar 127 travels to the left, to the distal side, whereas it comes to rest against the holding device 36 (distal side) after the specimen-collection chamber 71 has been opened. As the spindle sheath continues to rotate with the blade device, that is, in the attempt to open the specimen-collection chamber 71 wider, the clamping carriage is pulled toward the block 26, counter to the effect of the short coil spring, because the collar 127 rests against the holding device 36 on the distal side. Consequently, as will be described further below, the biopsy needle can be set into a back-and-forth movement that is superimposed by a limited angular-rotational movement of the biopsy needle to both sides. This angular-rotational movement is effected by the attempt of the blade sheath to carry the biopsy needle along in the rotation; the needle, however, is prevented from rotating past a predetermined angular rotation, as can be seen particularly in FIGS. 12*b* through 12*d*.

The gear 74 at the left end of the threaded spindle meshes with the toothed roller 23 after the biopsy-needle carrier has been inserted into the brackets 40. To allow the biopsy-needle carrier 37 to be inserted into the brackets of the clamping carriage when the carriage is not clamped (FIG. 2), the biopsy-needle carrier has two planar, parallel recesses 77 (FIG. 2). When the sliding surface of the biopsy-needle carrier 37 is placed onto the surfaces 41, 42 and 44, the biopsy needle is simultaneously inserted into the holding device 36 of the base block 8. On the left side of the gear, a slightly conical plastic disk 78 can be incorporated in order to improve the rotating capacity of the spindle drive, especially if the holding device 36 is serving as a support for clamping the clamping carriage. When the biopsy-needle carrier is inserted correctly, the carrier slides to the right, with the sliding surface 43, across the surfaces 42 and 41 as the clamping carriage is clamped. Because the specimen-collection chamber 71 is closed after the biopsy-needle carrier has been inserted, the gear 74 rests against the holding device 36.

If the toothed roller 23 is driven further in the same direction, the threaded-spindle drive screws the clamping carriage to the right, by way of the biopsy-needle carrier, until it is latched; in the process, the biopsy needle is retracted, while the blade sheath remains in its position. The blade sheath protrudes past the tip of the biopsy needle after the latching procedure. Therefore, after the clamping carriage has been latched, the blade sheath is rotated back into the initial position (opposite direction of rotation); the gear 74 is displaced from the left to the right in the toothed roller. After the clamping carriage has been unlatched, the biopsy needle and the blade sheath with the gear slide to the left again with the biopsy-needle carrier. Now the blade sheath can be displaced to the right again in order to open the specimen-collection chamber 71 until the collar 127 comes into contact. The function of the "floating" seating of the clamping carriage in connection with the controllable drive motor and the tubular piece 126 connected to the blade sheath and having the collar 127 is explained in greater detail in connection with the biopsy procedure.

A sealing element 76 produces a connection between the right end of the blade sheath and the hollow biopsy needle that permits rotation, but is airtight, so that air cannot enter between the biopsy needle and the blade sheath surrounding it coaxially, and air cannot exit under overpressure conditions. The sealing element 76 comprises a plastic hose that is pulled over the proximal end of the blade sheath. The inside diameter is selected such that it rests lightly against the outside diameter of the biopsy needle. When a vacuum is generated in the interior of the biopsy needle, and thus between the biopsy needle (outside) and the blade sheath (inside), the elastic plastic hose is pulled against the outside diameter of the biopsy needle. Provided that the biopsy needle is rotated relative to the blade sheath, the hose can serve as a restoring element (restoring spring). For rotating the biopsy needle slightly by means of the blade sheath, the biopsy needle is slightly deformed in the region of the sealing element 76, so it is oval-shaped at the deformed point 0 (FIG. 12*f*). When the blade sheath rotates, the biopsy needle is carried along by the deformation 0 until the rotation of the needle is limited by a stop (FIGS. 12*b* through 12*d*).

This angular-rotational movement of the biopsy needle simultaneously effects the pivoting of the sharpened longitudinal edges of the biopsy-needle space to both sides about the longitudinal axis of the biopsy needle. Because this angular-rotational movement is effected by the same drive and occurs simultaneously with the back-and-forth movement of the biopsy needle, the cutting edges of the specimen-collection chamber 71 sever the tissue, in the manner of a driven knife, both longitudinally in the X-axis and with an angular offset, so the tissue, which is under pressure (external and/or internal pressure) reliably enters the open specimen-collection chamber 71. FIG. 12*f* illustrates the specimen-collection chamber 71 in the neutral initial position after opening, FIG. 12*g* shows the position following an angular rotation to the right by the angle α, and the simultaneous retraction of the biopsy needle by the distance X1 (about 2 mm) to the proximal side; FIG. 12*h* shows the position of the biopsy needle during a rotation to the left by the angle β, and the simultaneous movement of the biopsy needle to the distal side by the distance X2 (about 2 mm). The movement of the cutting edges of the specimen-collection chamber 71 or the biopsy needle ensures that the tissue will be severed at the longitudinal edges, regardless of the tissue structure. The described movement of the biopsy needle, and therefore of the sharpened longitudinal edges of the specimen-collection chamber 71, also ensures that the severed piece of tissue will enter the specimen-collection chamber 71, even if the pressure that is normally exerted is absent.

A round, hollow plastic part 47 is placed onto the right end of the biopsy needle 2 in a frictional, airtight connection. At its left end, the plastic part 47 has a bearing element 49, which is pressed into the biopsy-needle carrier; at its right end, which protrudes from the hand piece, a further plastic part 112 is provided. This part can rotate relative to the plastic part 47 and the biopsy needle 2. An O-ring is inserted between the biopsy needle and the plastic part 112 to assure a seal. At its right end, the plastic part has a tappet 17, onto which the connecting element 4 is pushed to form an airtight connection. Also disposed at the right end protruding out of the biopsy-needle carrier and the housing is a knurled knob 80, which can be rotated to adjust the position of the specimen-collection chamber 71 radially without altering the position of the blade sheath. Only a single rotation of the specimen-collection chamber 71 is associated with a rotation of the biopsy needle. The plastic part 47 is pressed, with the biopsy needle, the blade sheath, the bearing element 49 and the threaded-spindle nut 75, into the biopsy-needle carrier. By way of the bearing element 49 and its narrow guide in the blade sheath, the biopsy needle is seated to rotate in the biopsy-needle carrier and in the blade sheath, and to be displaced with the biopsy-needle carrier along the longitudinal axis. As explained above, the blade sheath can be rotated axially relative to the biopsy needle.

To the right of the bearing element 49, a polygonal member 50 is disposed on the plastic part 47. The polygonal member can be clamped to latch with the biopsy-needle carrier 37, so the specimen-collection chamber 71 of the biopsy needle can be brought into and held in the position that is most favorable for the biopsy collection by means of the knurled knob 80. During the rotation, the two legs 39 of the biopsy-needle carrier, which comprises an elastic plastic, are spread by the corners of the polygonal member until the surfaces of the polygonal member are nearly perpendicular to the legs 39 again, and the polygonal member is latched again (FIG. 12*c*). The polygonal member is then adjusted by a predetermined increment. If the polygonal member is hexagonal, the rotational distance is 60°; if more rotational increments are desired, a polygonal member having 8, 10, etc., sides should be selected accordingly.

As can be seen particularly in FIGS. 12*b* through 12*f*, the biopsy-needle carrier has two legs 39, which are connected to one another by a cap element 116. In the plastic carrier, the polygonal member 50 of the plastic part is seated to be latched: The legs 39 connected to the elastic fastening element are first spread apart during a rotation in order to return to their initial position due to the elasticity. If the inscribed circle diameter S selected for the polygonal member is smaller than the distance A (clear width) of the two legs from one another, the biopsy needle can rotate slightly to both sides about its axis, by a predetermined angle (α or β) (FIGS. 12b-12d illustrate the center position). The legs 39 of the biopsy-needle carrier are not spread here; on the contrary, they prevent the biopsy needle from rotating by a larger angle, because the drive is configured such that the blade sheath can be rotated further, but the resistance of the leg limit is greater than the drive moment. The corners of the polygonal member impact the legs 39, and prevent a further rotation, because the torque acting on the biopsy needle does not suffice to spread the two legs. Because the plastic part 47 with the polygonal member is permanently connected to the needle, and the blade sheath was pushed onto the deformed region 0 of the biopsy needle when the specimen-collection chamber 71 was opened, and the sealing element 76 enters a frictional connection with the outside of the biopsy needle when the specimen-collection chamber 71 is open, when the blade sheath is driven in a respective direction of rotation, the biopsy needle also rotates about its axis due to this frictional connection until the stop effected by the polygonal member prevents a further rotation in the absence of a greater torque.

Because the vacuum that dominates in this phase pulls the elastic sealing element more strongly against the outside surface of the biopsy needle, the sealing element facilitates the rotation of the blade sheath relative to the biopsy needle, on the one hand; on the other hand, the sealing element acts as a restoring element if lightly touched. This limited rotational movement is understood to be an angular-rotational movement. The biopsy needle, which can rotate to a limited extent, ceases its angular-rotational movement due to the change in the direction of rotation, and returns to its initial position because of the twisted sealing element, then is rotated in the other direction counter to the effect of the elastic sealing element. Generally, about one rotation of the gear 74 in each direction (about one rotation from the zero position) suffices for the limited angular-rotational movement in connection with the back-and-forth movement, as described above. When the gear rotates, the biopsy needle is displaced from the zero position by about 2 mm to the left or right, and is simultaneously moved about the longitudinal axis by the angle α or β. Generally, this movement is repeated about five times in each direction.

Figure 12:
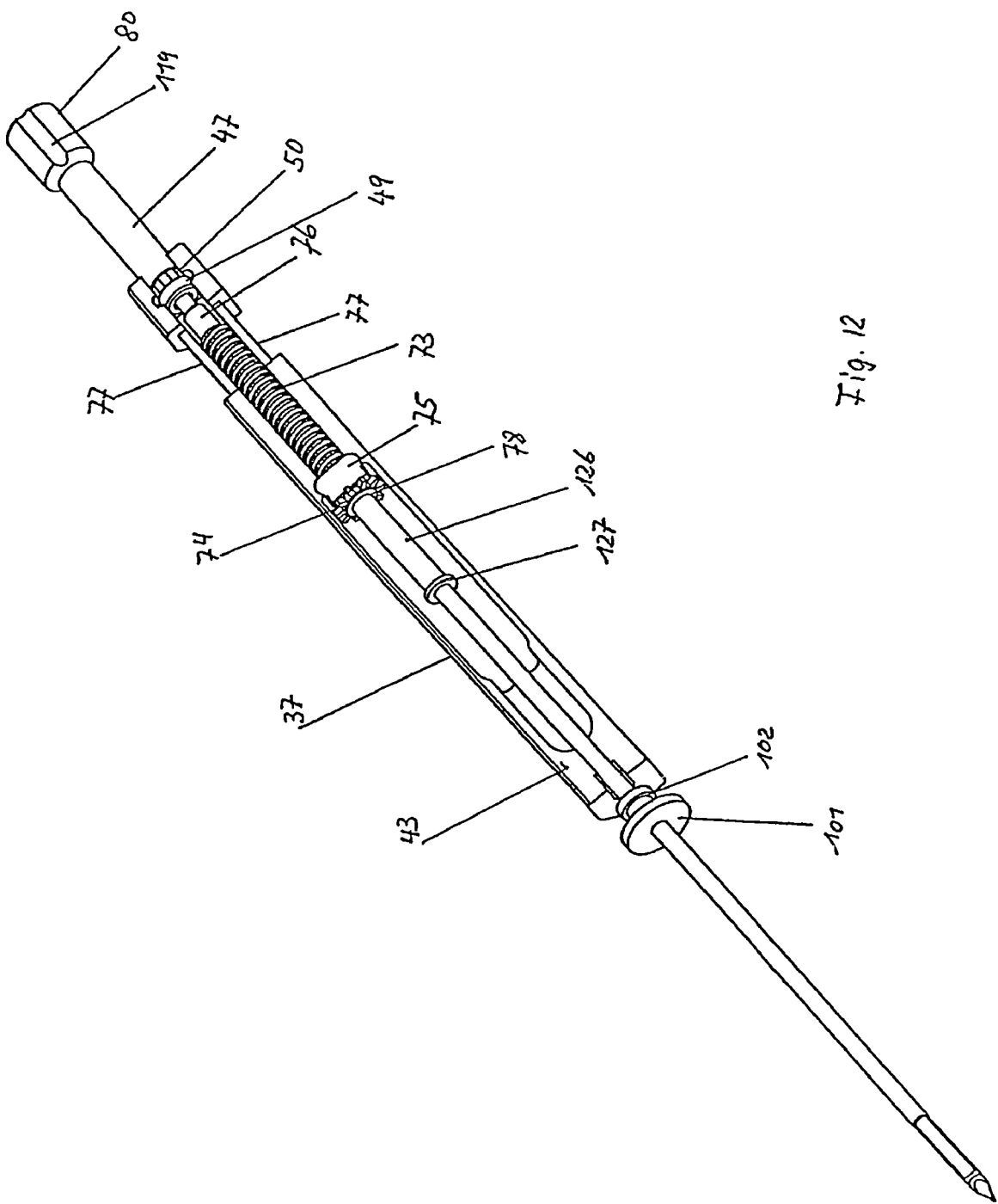
FIG. 12 depicts the biopsy needle carrier with biopsy needle/cutting sleeve pressed and plastic component pressed in (from below, rotated by approximately 90°, perspective view).
Figure 12F:
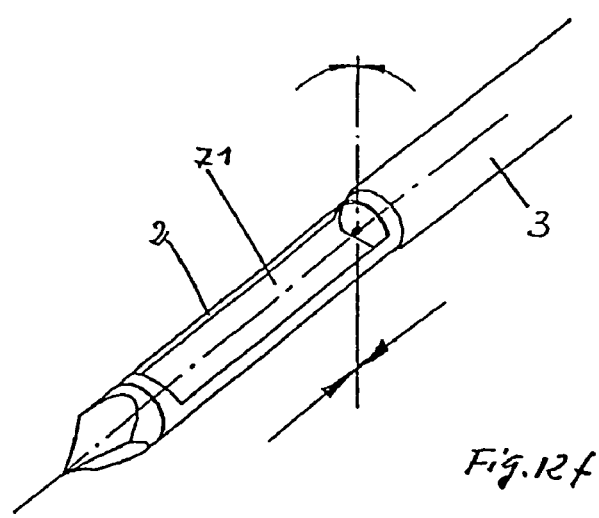
FIG. 12f depicts the distal side of the biopsy needle with sample removal chamber and cutting sleeve in basic position, corresponding to the position of the multiple edge in FIG. 12c.
Figure 12G:
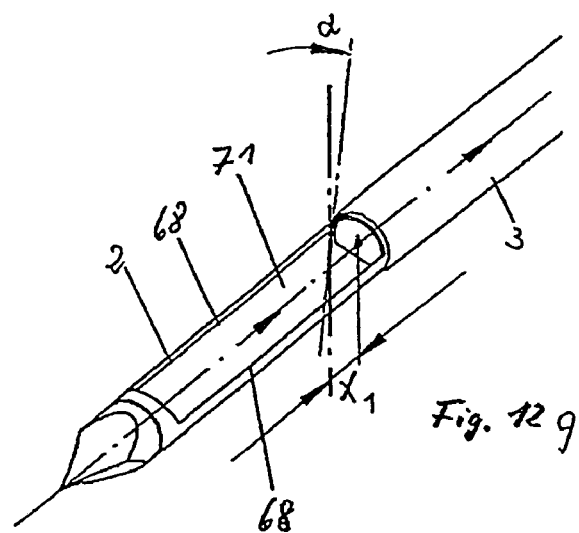
FIG. 12g depicts the biopsy needle as depicted in FIG. 12f, with pivoting of the sample removal chamber to the right and advanced cutting sleeve, corresponding to the position of the multiple edge as depicted in FIG. 12d.
Figure 12H:
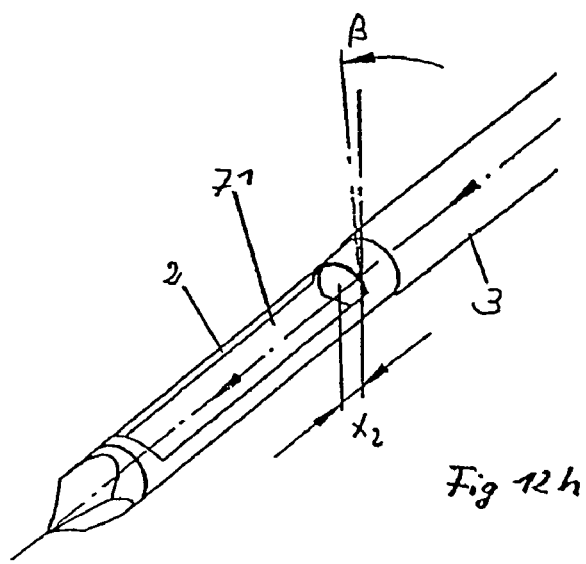
FIG. 12h depicts the biopsy needle as depicted in FIG. 12f, with pivoting of the sample removal chamber and retracting cutting sleeve corresponding to the rotation of the multiple edge as depicted in FIG. 12b.

As shown particularly in FIG. 12, the blade sheath surrounding the biopsy needle coaxially is connected to the biopsy-needle carrier 37 by way of the threaded-spindle nut 75. The threaded-spindle sheath 73 is seated so as to rotate in the threaded-spindle nut 75. A rotation of the gear 74 by the drive motor of the toothed roller 23 causes the biopsy-needle carrier and the clamping carriage to be moved to the right as soon as the gear 74 comes into contact with the holding device 36. When the gear occupies a position within the length of the toothed roller 74, that is, provided that the gear is free and does not rest against the holding device or the threaded-spindle nut 75, the blade sheath can be adjusted alone, for example after the biopsy needle has been clamped, in order to align the needle tip and the blade sheath for returning the blade sheath to the initial position, or for opening and closing the specimen-collection chamber 71.

When the specimen-collection chamber 71 is opened, the blade sheath is pushed over the slightly deformed region 0 of the biopsy needle. In this position, as the blade sheath continues to rotate, the biopsy needle is carried along in the direction of rotation by a predetermined angle; because the connection between the blade sheath and the biopsy needle only permits the transmission of a predetermined torque, however, the rotational movement of the biopsy needle comes to a halt when the corresponding corners of the polygonal member come into contact with the legs of the biopsy-needle carrier (FIGS. 12b and 12d). The tubular piece 126 with the collar 127, which is mounted to the distal side of the gear, and cooperates with the holding device 36, serves in setting the needle into a brief vibrating movement (back-and-forth movement), in cooperation with the control, and in simultaneously setting the biopsy needle into an alternating angular-rotational movement, as described above.

Because the vibrating (back-and-forth) movement is effected by the drive for the blade sheath 3, the connection of the blade sheath to the deformed point 0 of the biopsy needle and the configuration of the polygonal member 50 and the biopsy-needle carrier simultaneously effect a limited rotation of the biopsy needle in both directions of rotation (depending on the direction of rotation), which is superimposed over the back-and-forth movement of the biopsy needle. These two combined movements sever any type of tissue with the cutting edges of the specimen-collection chamber 71. The tissue, even if it is tough or has inclusions, can be reliably pulled or inserted into the specimen-collection chamber 71 with or without pressure. The aforementioned vibrating (back-and-forth) movement of the biopsy needle, which also effects the angular-rotational movement, is described below:

When the toothed roller is driven, the gear 74 opens the specimen-collection chamber 71 until the collar rests against the distal side of the holding device 36. If the same direction of rotation is maintained, and the gear no longer rests against the threaded-spindle nut, the further rotation causes the clamping carriage to be pulled over the biopsy-needle carrier toward the block 26, counter to the effect of the short coil spring, because the contact of the collar 127 with the distal side of the holding device 36 makes it impossible for the blade sheath to be opened further. The clamping path or the movement path (X1 or X2) is about 2 mm, or corresponds to about one rotation of the blade sheath.

When the gear 74 stops against the threaded-spindle nut, the direction of rotation of the motor is reversed and, with the support of the short coil spring, the clamping carriage returns to its initial position (resting position), and the biopsy needle is rotated back into its zero position. Because a detector counts the motor rpm, and the actual values are stored in a programmable microprocessor, corresponding preset commands can be used to change the direction of rotation of the motor, so the clamping carriage is pulled toward the block again or retracted after being released. The continuous reversal of the motor's direction of rotation, as specified in advance, works in conjunction with the clamping and release of the carriage to effect a back-and-forth movement of the biopsy needle that is superimposed with a limited angular-rotational movement of the biopsy needle to both sides, depending on the direction of rotation. Five back-and-forth movements typically suffice to assure a good specimen collection, even of tough tissue or tissue having inclusions, such as calcification. The back-and-forth movement of the biopsy needle, in conjunction with the limited angular-rotational movement of the needle, and the sharpened cutting edges, severs the tissue, which has been pulled to the specimen-collection chamber 71 by a vacuum, for example, at the side edges in order to permit or greatly facilitate the entrance of the specimen into the specimen-collection chamber 71, even if the specimen comprises tough tissue.

The described movement of the biopsy needle, and thus of the sharpened longitudinal edges of the specimen-collection chamber 71, permits a superior severing of the tissue after or during the opening of the specimen-collection chamber 71. The same good tissue-severing action can be attained if this vibrating movement or angular-rotational movement is performed during the opening process, that is, when the blade sheath is retracted. FIGS. 12g and 12f illustrate this superimposed movement of the biopsy-needle space in detail, in the phases of left and right rotation as well as the zero position. FIG. 12g and others depict the initial position: The biopsy-needle space is open, the blade sheath is retracted by about 2 mm past the proximal edge of the specimen-collection chamber 71, and the polygonal member is in the neutral position (FIG. 12c). In the representations of FIGS. 12h and 12g, the biopsy needle is retracted into the blade sheath, and the needle is simultaneously pivoted by the angle α. FIGS. 12f and 12d show the other direction of rotation, and the rotation by the angle β. The proximal edge of the biopsy-needle space is displaced by about 2 mm toward the distal side relative to the initial position, and is simultaneously pivoted by the angle β in the other direction. FIGS. 12g, 12f and 12b through 12d illustrate a cycle that is repeated several times—typically five times—under the control of the microprocessor. This back-and-forth movement and the limited angular-rotational movement can be effected by electrical elements that are connected to the needle or the clamping carriage.

FIGS. 11a through 11g illustrate details about the specimen-collection chamber 71 and the embodiment of the biopsy-needle tip. Approximately 25% of the cross-section of the specimen-collection chamber 71 adjoining the needle tip 70 is open to the top. For example, if the biopsy needle has an outside diameter of 3.3 mm, the height H of the specimen-collection chamber 71 is about 2.3 mm. The specimen-collection chamber 71 is approximately between 15 and 25 mm long. Adjoining the chamber is the hollow space of the biopsy needle. At the transition, that is, at the proximal end of the specimen-collection chamber 71, the cross-section of the hollow space of the biopsy needle is closed by between 50% and 75% by a narrowed region, such as a stopper 79 (FIGS. 11b through 11e). The height of the stopper is selected such that the stopper extends downward past the recess for the specimen-collection chamber 71.

As can be seen in FIG. 11e, an opening F is provided in the floor of the specimen-collection chamber 71; if the inside diameter of the needle is 3.0 mm, the height of the opening is 0.6 mm. The vacuum is intended to pull the tissue specimen into the specimen-collection chamber 71 as the chamber is continuously opened, and bring the specimen into contact with the wall of the chamber. If an overpressure is present in the biopsy-needle hollow space, the narrowed region, the stopper, increases the pressure. The stopper is about 10 mm long, and is glued or welded into the hollow space. The use of laser welding has revealed that it is advantageous to construct the left side of the stopper by removing material at the end face to make it short, namely about 2 mm long. Consequently, in this region at the end face, the tube of the biopsy needle is welded completely to the end face of the stopper, and is airtight at the end face. The stopper can also be shorter, provided that the same effect is attained. The stopper can also be replaced by a lip or a latch of approximately the same height.

It is critical that the narrowed region be embodied to allow the vacuum in the specimen-collection chamber 71 to be effective from the floor, so that the specimen sticks to the wall of the chamber as the blade sheath is closed, that is, during the cutting process, and does not change its position. It has also proven advantageous to provide additional securing means on the specimen-collection wall. Sucking the specimen into the specimen-collection chamber 71 from below results in a high filling capacity of the specimen-collection chamber 71, on the one hand, and the configuration of the chamber, in particular, allows the specimen to be secured well to the wall, on the other hand. For this reason, it is crucial that the lateral severing of the tissue through the described movement of the sharpened longitudinal edges of the specimen-collection chamber 71 ensures that the tissue reaches the chamber floor.

Because the blade sheath severs the specimen on the outside of the biopsy needle, the process of suctioning the specimen in the inside is also maintained during a severing process, if possible. The outside location of the blade sheath, and the fact that the tissue sticks to the inside floor of the specimen-collection chamber 71, prevent the specimen from being rotated or twisted by the rotating longitudinal movement of the blade sheath during the closing process. The quality of the specimen is greatly improved over systems that employ a twisting effect. The pathologist obtains a starting material whose cross-section corresponds to the section in the tissue, not a twisted or deformed mixture of tissues. Ejecting the specimen under pressure is a reliable method of depositing it. The stopper 79 permits this. In addition, the specimen-collection chamber 71 is completely cleaned, so if the biopsy is repeated, there is no mixing of tissue specimens (residual particles).

Because the vacuum-generating device is simultaneously used as a pressure-generating device, the entire hollow space, particularly the biopsy needle, is cleaned during the ejection process. For normal tissue, it suffices to use the wall thickness of the biopsy-needle tube, which is about 0.15 mm, as a lateral cutting edge. For hard and/or tight tissue, the filling capacity achieved in the specimen-collection chamber 71 solely through vacuum suction is insufficient, because the tissue at the side edges is not adequately severed. Through the embodiment of the long sides of the specimen-collection chamber 71 as cutting edges 68, as can be seen particularly in FIGS. 11g and 11f, the superimposing of a repeated back-and-forth movement and a limited, repeated angular-rotational movement of the biopsy needle with the specimen-collection chamber 71 to the left and right (as described), as well as the pressure effect of, for example, an internal vacuum, for example with the ultrasonic head, the specimen tissue is severed longitudinally, so the specimen travels to the floor of the specimen-collection chamber 71 far better because of the vacuum or external pressure. The exertion of an external pressure or an internal vacuum in the biopsy-needle hollow space can reinforce the cutting effect of the longitudinal edges.

Severing the long-side cutting surfaces of the tissue specimen to be removed through the movement of the needle attains a superior filling capacity, even with hard and/or leathery tissue or tissue having inclusions. This method provides adequate tissue material for testing. The cutting edge at the long side of the specimen-collection device is formed by the milling off of the partial piece (T1) from the wall thickness (FIG. 11g). The diameter (ra) of the outside contour of the biopsy-needle tube is retained, while the inside diameter (ri) of the inside contour changes over to the outside contour, via a perpendicular wall, through the milling out of the partial piece (T1) (FIG. 11g). FIG. 11d shows the closed specimen-collection chamber 71, in which the collected specimen is located. During the severing process, it has proven advantageous to move the blade sheath 78 out of its end position, shown in FIG. 11d, and about 2 mm in the distal direction, and then retract the blade sheath by these 2 mm into its end position. This shearing effect reliably severs fibers that may not yet be completely severed, which further increases the quality of the specimen.

The biopsy needle described here operates with a vacuum that is generated internally. The back-and-forth movement combined with the superimposed, limited angular-rotational movement of the biopsy needle, and thus of the blades of the specimen-collection chamber 71, also produces superior results in biopsy needles without a vacuum or if the vacuum fails, especially if, for example, an external pressure is exerted onto the tissue in the biopsy hollow needle, such as through ultrasound, instead of the internal vacuum. Using only the angular-rotational movement, superimposed with the back-and-forth movement of the needle in conjunction with the long edges of the specimen-collection chamber 71 embodied as blades, however, considerably improves the tissue-severing process and facilitates the entry of the tissue specimen to be cut out into the specimen-collection chamber 71. It must also be pointed out that the elastic sealing element is not required as a restoring element in every case; merely reversing the direction of rotation can effect the restoring action.

Figure 13:
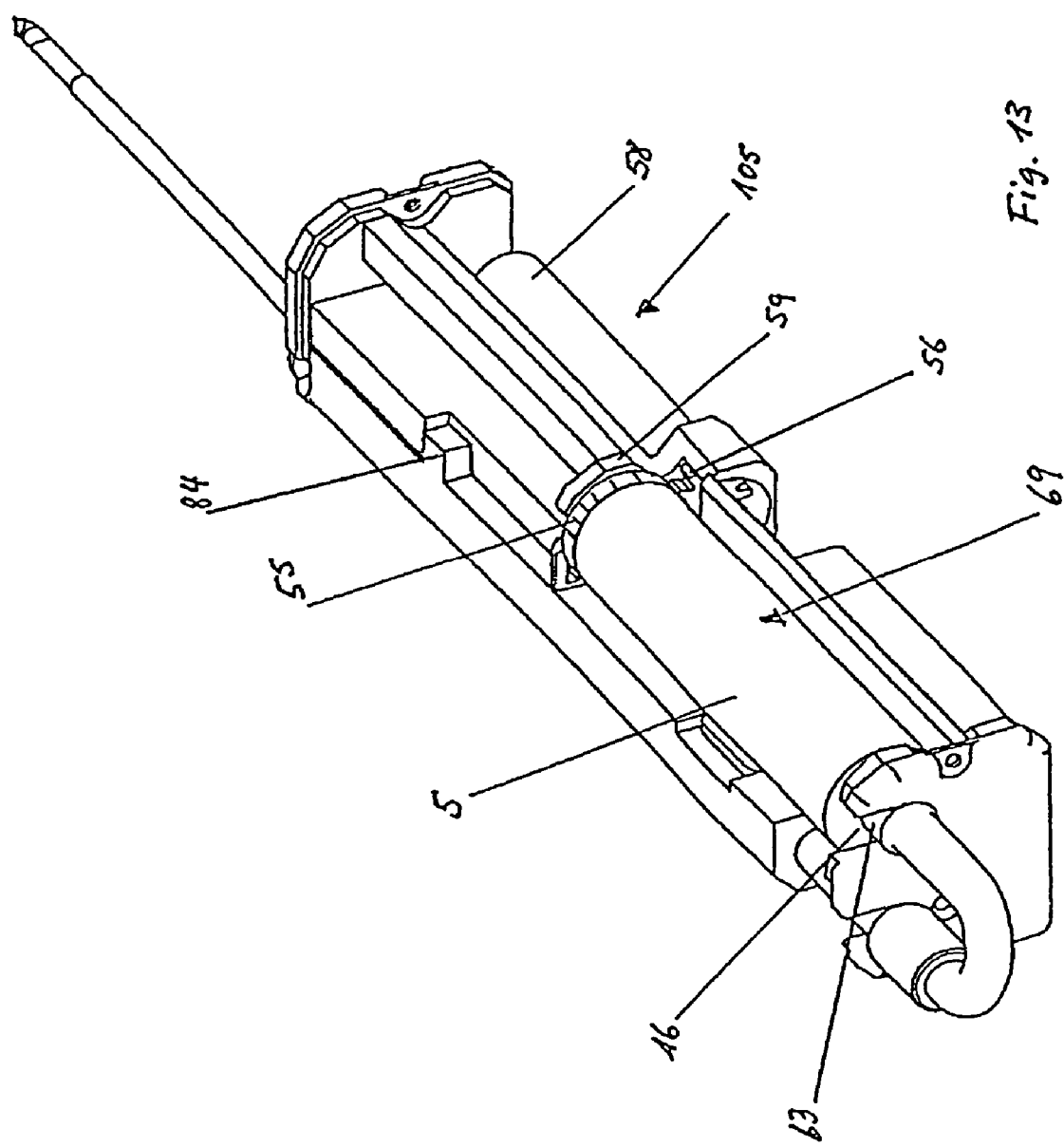
FIG. 13 depicts the vacuum-pressure device, installation and drive (viewed from behind, perspective view).

FIG. 13 shows the drive and the installation of the vacuum- and pressure-generating device 5 (view from behind, that is, along the Z-axis; housing lid and lower housing part omitted). In the upper, rear, right region, the vacuum- and pressure-generating device 5 is embodied as a plunger/cylinder unit 69. It comprises a syringe body 52 having a threaded spindle 53 inside it; at its end facing the bottom 51 of the syringe, a plunger 54 with sealing elements—a standard feature of syringes—is secured to the spindle (FIGS. 14a through 14d). At the end of the syringe body 52 facing the base block 8, a threaded-spindle nut 48 having a gear 55 at its circumference is disposed on the threaded spindle. The threaded-spindle nut has one or more thread turns. The threaded spindle 53 cooperates with the threaded-spindle nut 48. The spindle has a pitch of about 5 mm per turn, so with each rotation by means of the spindle drive, the plunger moves by a precisely defined distance out of the syringe body, that is, away from the bottom 51 of the syringe, or toward the bottom of the syringe, depending on the direction of rotation.

The gear rim 55 disposed at the circumference of the threaded-spindle nut meshes with the drive pinion 56, which is secured to the power takeoff shaft of the DC gear motor 58. The power takeoff shaft of the DC gear motor 58 is seated in the base block 8; for this purpose, the power takeoff shaft is inserted into the transverse plate 59 of the base block. When the DC gear motor 58 is activated, the plunger is moved toward the bottom of the syringe, or in the direction of the base block 8, depending on the direction of rotation. A DC motor having a high rpm is used as the drive motor; a planetary gear having a high step-down is disposed downstream of the DC motor. The motor corresponds to the motor described above for the clamping device. Hence, a counting device, comprising a two-armed blade wheel 131 and a photocell that is mounted to the motor side, is likewise secured to the distal side of the DC gear motor. The counting device is connected to the programmable microprocessor, so the function of the vacuum- and pressure-generating device can be controlled with the rpm: After an initial value has been ascertained, the functions can be called up with programmable or programmed specifications.

Figure 14:
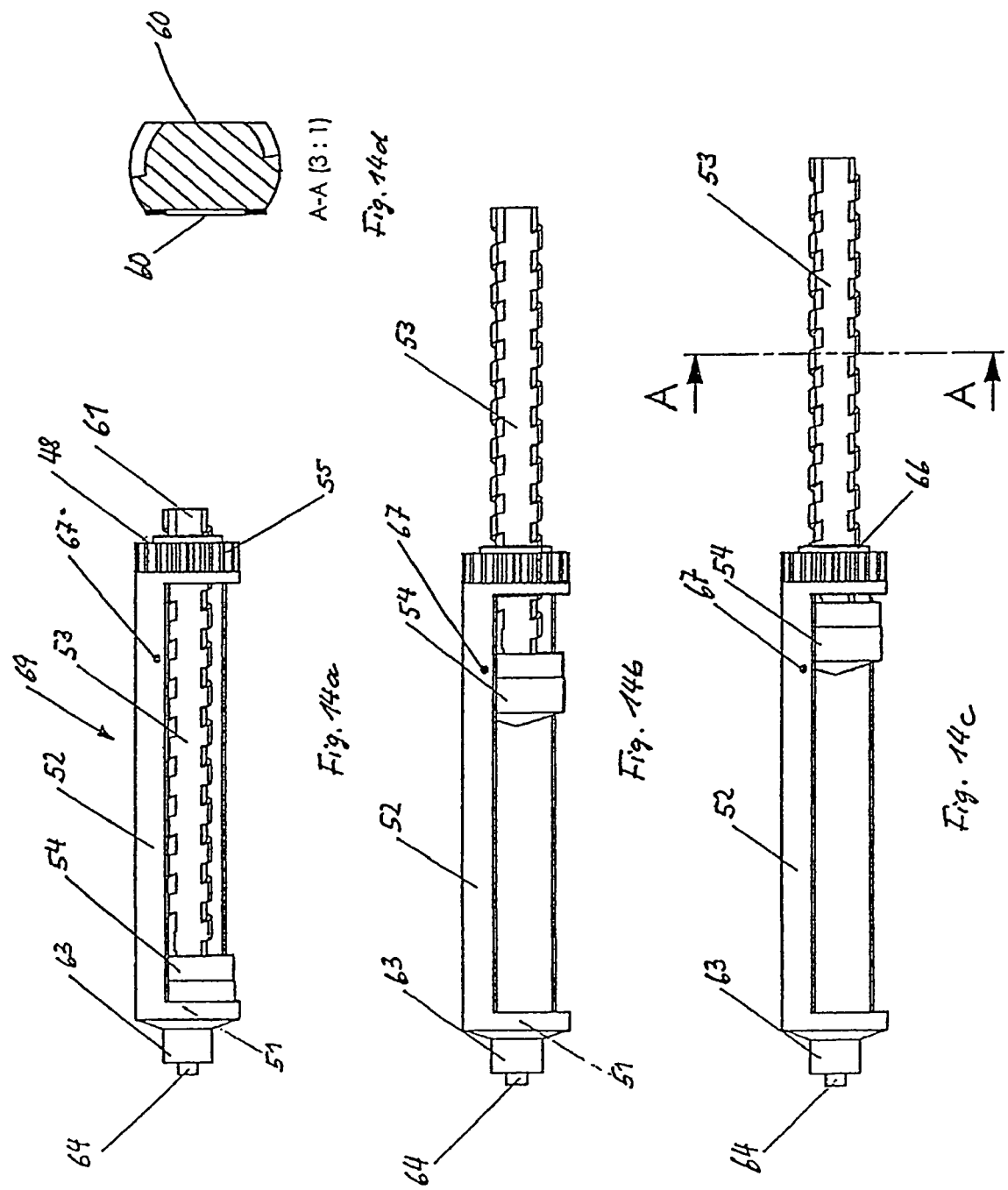
FIG. 14a depicts the vacuum-pressure device, with piston mounted on the syringe base (starting position for vacuum generation and end position for pressure generation, partial section).
FIG. 14b depicts the vacuum-pressure device with retracted piston; end position of the vacuum stroke of the piston (partial section).
FIG. 14c depicts the position of the piston following clearing of the ventilation hole; pressure balancing position (partial section).
FIG. 14d depicts section A-A through the threaded spindle in FIG. 14c.

The plunger 54 is embodied in a known manner as a syringe plunger. The plastic syringe body, a cylinder with a floor, is transparent. To prevent the threaded spindle 53 from rotating when the threaded-spindle nut is driven, the two oppositely located surfaces 60 of the threaded spindle are planar (FIG. 14d). The threaded spindle is inserted into the insertion element by its free end. The spacing of the threaded-spindle surfaces corresponds to the width of the U-shaped insertion element 62 of the base block 8. Only a small amount of play exists between the U-shaped cross-section of the insertion element and the spindle surfaces on both sides. The threaded-spindle nut is supported on the base block. To prevent the syringe body 52 from sliding out when the threaded-spindle nut rotates, the contact surface of the base block 8 has a slightly conical shape at the bottom. The connector 63 of the syringe body 52 is inserted into the passageway 16 of the housing end lid 7 such that the syringe body is held in an approximately horizontal position.

To make the rotation of the threaded spindle smooth, the threaded-spindle nut with the gear rim has an approximately 1.5-mm thick phase 66 (FIG. 14c) on the side facing the base block. Because the surface of the rib 59 on the base block 8, which cooperates with the phase 66 of the threaded-spindle nut 48, is inclined from top to bottom, the vacuum- and pressure-generating device 5 is pulled down during operation. To generate a sufficient vacuum of about 200 hph in the specimen-collection chamber 71, if the biopsy-needle length is about 250 mm and the inside diameter of the biopsy hollow needle is between 3 and 5 mm, a 20-ml syringe body having a length of about 90 mm is used. To also be able to use the syringe body to generate pressure, a ventilation bore 67 having an approximately 1.5-mm diameter is provided after about ¾ of the length, corresponding to the stroke for generating the vacuum (position according to FIG. 11b). The ventilation bore can also be embodied as an oblong slot.

When the vacuum is no longer required, and the syringe plunger is moved past the ventilation bore 67 (FIG. 14c), the supply of air (atmospheric pressure) via the ventilation bore 67 reduces the vacuum that was previously built up in the biopsy hollow needle. If the direction of rotation of the gear motor is then reversed, the depression of the plunger (toward the bottom of the syringe) causes the vacuum- and pressure-generating device to effect the buildup of an overpressure in the system, so the specimen is ejected after the specimen-collection chamber 71 is opened. To prevent tissue fluid from escaping during the brief opening of the ventilation bore 67, the ventilation bore may be covered with an air-permeable sponge (not shown), for example. A delay circuit that is integrated into the control mechanism prevents the tissue specimen from being ejected through the inadvertent depression of the programming key 89; the delay circuit only initiates the procedure after the key has been held down for about 1.2 to 1.5 seconds. The specimen cannot be ejected until the biopsy needle has been removed from the tissue. Moreover, the compressed air not only cleans the specimen-collection chamber 71, but particularly the interior of the biopsy needle as well.

The stopper that narrows the needle hollow space impedes or completely prevents the entry of tissue segments into the biopsy-needle hollow space. The narrowing of the needle hollow space by the stopper 79 increases the pressure at the specimen-collection chamber 71, and therefore improves the ejection of the specimen when the specimen-collection chamber 71 is only half-open. In the use of the vacuum biopsy device, it is advisable to use a specially designed coaxial cannula that is tailored to the specifications and requirements of the device. The cannula must contain corresponding devices that prevent or preclude the entrance of air and the exit of tissue fluid; on the other hand, it should be able to be inserted easily into the tissue. The operation of the biopsy device is explained in detail below.

The following segments of the procedure are performed extensively automatically after being initiated: a) starting and setting the initial position; b) clamping the biopsy needle and injecting it into the tissue; c) cutting the specimen out of the tissue (specimen collection); and d) removing the specimen after the closed biopsy needle has been removed from the tissue.

a) Starting and Setting the Initial Position

The removable insertion element 20, comprising the vacuum- and pressure-generating device, the elastic connecting element and the biopsy-needle carrier with the needle and the blade sheath, and further elements connected thereto, and a guide roller 81 that is placed onto the needle are delivered in sterile packaging. The removable elements (FIG. 2) are held by an insertion aid that is removed after the elements have been inserted into the hand piece. This insertion aid 104 has two grips for grasping the top, and brackets 108 for holding the biopsy-needle carrier 37 and the vacuum- and pressure-generating device. To secure the vacuum- and pressure-generating device in its position (parallel to the biopsy-needle carrier), a pin 110 provided on the bracket-holding device is inserted into the ventilation bore.

The plunger 54 in the syringe body 52 is raised slightly (1 to 2 mm) from the bottom of the syringe, and the specimen-collection chamber 71 of the biopsy needle 2 is opened to allow visual checking of the specimen-collection chamber 71 prior to insertion. After the housing lid 10 has been opened, the biopsy-needle carrier, including the biopsy needle 2, the cutting device 3 and other connected parts, such as the vacuum- and pressure-generating device 5 connected to the connecting element 4, are inserted into the connecting elements provided on the hand piece (FIG. 2). During the insertion process, it must be ensured that the gear 74 meshes with the teeth of the toothed roller 23. The blade sheath is inserted from above into the U-shaped holding device 36; at the same time, the brackets 40 of the clamping carriage are guided into the recesses 77 of the carrier element, and the guide roller 81 is inserted into the passageway 13, so it surrounds the flanks 101 and 102 of the housing end lid 6. The blade sheath can be longitudinally displaced in the guide roller, and is seated to rotate freely; the guide roller itself, however, can no longer be displaced relative to the blade sheath following insertion into the housing end lid.

On the one hand, the vacuum- and pressure-generating device is then inserted by the free end 61 into the insertion element 62 of the base block 8, which is open to the top, and into the U-shaped passageway 16, which is open to the top, by the connector 63, on the other hand. The connector 63 lies above the switching pin 19. Because the insertion element on the side of the base block has a clear width that just permits the insertion of the threaded spindle provided on both sides with surfaces 60, the threaded spindle is held, fixed against relative rotation, in the insertion element. The gear rim 55 of the threaded-spindle nut 48 engages the drive pinion 56 of the gear motor after the insertion. The spacing between the base block and the housing end lid 7 is maintained to allow space for the syringe body 52 with the threaded-spindle nut 48 placed on the syringe body. The unit formed by the syringe body and the gear placed on it is held such that it cannot be axially displaced.

After the insertion, the vacuum- and pressure-generating device lies parallel to the biopsy-needle carrier and the connecting element 4 describes a curve of about 180°. It should be noted that the insertion takes place when the clamping carriage is not clamped. This means that the gear 74 engages the right end of the toothed roller when the specimen-collection chamber 71 is open (FIG. 3). After proper insertion, the housing lid can be closed. The described insertion aid can be employed to facilitate the insertion process. The insertion can also take place without the insertion aid, however.

When the housing lid is closed, the connector 63 is pressed down, thereby actuating the microswitch by way of the switching pin 19 installed in the housing end lid. This activates the electrical system, which is indicated by the blinking reset diode (yellow) 91 on the front of the hand piece. The reset diode blinks yellow, which means that the positioning procedure for the individual elements, i.e., the insertion procedure, has not ended yet; the DC gear motor 21 must first close the specimen-collection chamber 71 with the blade sheath 3 (the specimen-collection chamber 71 was partially open during the insertion). This is effected by the rotation of the threaded sheath connected to the blade sheath. The blade sheath moves to the left until the gear 74 comes to rest near the inside of the holding device 36.

After the specimen-collection chamber 71 has been closed, the plastic disk 78 rests against the holding device 36 (inside). During this process, or before or after it, the DC gear motor 58 brings the syringe plunger 54 into contact with the bottom 51 of the syringe. In this phase, the counters of the microprocessor for the movement of the biopsy needle/blade sheath unit and the vacuum- and pressure-generating device are set at zero. From this initial position, the programmed movements are executed by way of the counting devices disposed on the two motors. After the initial positions for the vacuum- and pressure-generating device and the biopsy needle/blade sheath unit have been reached, the clamping diode 94 and the specimen-collection diode 92 illuminate (yellow and green, respectively), and the reset diode goes out.

b) Clamping the Biopsy Needle and Injecting the Biopsy Needle into the Tissue

In this phase, the operator must decide whether to initiate the clamping of the clamping carriage, or to collect a further tissue specimen after a first specimen has been collected, for example. When collecting a first tissue specimen, the operator depresses the clamping key 90. This initiates the clamping of the clamping carriage; the clamping diode blinks yellow, and the specimen-collection diode (green) 92 goes out. The depression of the clamping key (because of the delay circuit, the key must be held down for about 1.2 to 1.5 seconds) effects the supply of current to the electrical DC gear motor 21, which drives the toothed roller 23. The gear 74 that meshes with the toothed roller 23 rotates the spindle shaft, and simultaneously the blade sheath 3 connected thereto.

Because the spindle nut 75 is pressed into the biopsy-needle carrier 37, and the gear 74 is supported against the holding device 36 by the plastic disk 78, the holding device being permanently connected to the housing by the base block 8, the rotation of the threaded-spindle sheath 73 causes the biopsy-needle carrier to move to the right. At the same time, the biopsy needle 2 connected to the biopsy-needle carrier via the bearing element 49 is carried along, which causes the tip of the biopsy needle to move into the blade sheath. The biopsy-needle carrier 37 is displaced to the right by way of the recess/bracket connection of the clamping carriage, and counter to the effect of the coil spring 31, until the spring 34 presses the lever 33 of the latching element into the recess 82 of the clamping carriage. The clamping carriage is locked in this position.

The gear motor receives the control command that the locked position has been reached, for example by way of a photocell that is recessed into the sliding surface of the cover plate and cooperates with the retracted biopsy-needle carrier, or by way of the microprocessor, which compares the actual rpm to the entered desired number, which was preprogrammed. The direction of rotation of the motor is reversed after the desired value has been attained, and the blade sheath is rotated back to the right by the distance that the blade sheath traveled past the biopsy-needle tip due to the displacement of the clamping carriage and the biopsy needle. At the end of this step, the blade sheath completely closes the specimen-collection chamber 71 (FIG. 11*d*), as at the beginning of the clamping process. The locking diode 95 illuminates green; the clamping diode 94 stops blinking. To reduce the frictional force between the gear and the support element during the clamping process, an additional plastic disk 78 is disposed between the gear 74 and the holding device 36, for example.

Now the biopsy needle of the biopsy device is inserted into a coaxial cannula that has been positioned in advance, for example. The proximal end of the positioned coaxial cannula has a seal that is dimensioned such that it seals the space between the blade sheath and the cannula, but permits the biopsy needle to be inserted easily with the blade sheath. The sealing ring prevents air from being sucked in from the outside via the space between the cannula and the blade sheath. Likewise, the sealing ring prevents the escape of fluid (cytological material) after the biopsy needle has been inserted or injected. Thus, it is virtually impossible to contaminate the disinfected hand piece, on the one hand; on the other hand, the flank 101 of the sterile guide roller 81 prevents the hand piece from becoming contaminated from the cannula. The tip of the biopsy needle is guided up to the swelling through the removal of the mandrel in the coaxial cannula and, after being positioned correctly, is injected into the swelling.

The injection is initiated by the depression of the actuating key 88. The depression of the key causes the clamping carriage to be released due to the pivoting of the two-armed lever 33 about the shaft 35. The clamping carriage is thrown to the left by the spring action. The initiation of the injection and the new needle position are reported to the microprocessor, for example by an integrated photocell. The specimen-collection diode illuminates green, and the clamping diode illuminates yellow.

c) Cutting the Sample Out of the Tissue

A further depression of the programming key 89 initiates the specimen-collection procedure; the specimen-collection diode 92 blinks green. First, the DC gear motor 58 of the vacuum- and pressure-generating device is activated. The plunger of the vacuum- and pressure-generating device is moved in the direction of the base block, i.e., away from the bottom of the syringe, until it reaches a position shortly before the ventilation bore 67 is uncovered (FIG. 14*b*). The vacuum is generated in the system. After the end position has been attained, the system activates the motor 21, and the gear/spindle drive opens the blade sheath, which seals the specimen-collection chamber 71. During the opening process, the tissue and possible cytological fluid (cytological material) are supposed to be sucked or pressed into the specimen-collection chamber 71 due to the vacuum that dominates in the system, or an externally exerted pressure. Cytological fluid is sucked into the biopsy-needle hollow space through the vacuum, among other things, and flows into the vacuum- and pressure-generating device.

It has proven advantageous that the stopper 79 diverts the vacuum primarily toward the lower region, the lower side, of the specimen-collection chamber 71, and the stopper 79 impedes or prevents the penetration of tissue into the biopsy hollow needle. After the specimen-collection chamber 71 has been completely opened, or during the opening process, the biopsy needle is moved briefly back and forth about five times in a region of approximately 2 mm. In a preferred embodiment, the biopsy needle and thus the specimen-collection chamber 71 simultaneously perform an angular-rotational movement about the longitudinal axis. This movement is effected when the microprocessor issues the drive motor 21 the command to open the specimen-collection chamber 71 wider when the chamber is already completely open; this is impossible, because the collar 127 prevents a further displacement of the blade sheath to the right.

The connection between the threaded spindle/threaded-spindle nut and the biopsy-needle carrier element causes the clamping carriage to be displaced to the distal side by about 2 mm, thereby compressing the short coil spring. After a predetermined rpm that corresponds to the distance of 2 mm has been attained, the microprocessor control system reverses the direction of rotation of the drive motor. The coil spring and the motor return the clamping carriage to its initial position. This action reverses the drive motor again, and the clamping carriage is again pulled counter to the effect of the short coil spring; after the clamping path has been traversed, the reversal is effected, and so on. Because of this back-and-forth movement, and the associated angular rotation of the biopsy needle, the tissue is severed by the longitudinal edges of the specimen-collection chamber 71, and the specimen is reliably inserted into the specimen-collection chamber 71, even if the tissue is tough. The procedure can be repeated an arbitrary number of times, depending on the programming. Generally, five cycles suffice to control the sharpened long sides of the specimen-collection chamber 71 to sever the lateral tissue of the tissue specimen, even if the tissue is hard or has inclusions, and to insert the specimen, easily and completely, into the specimen-collection chamber 71, for example using a vacuum.

It is emphasized here that, in the simplest case, the severing of the tissue can also be performed exclusively through the back-and-forth movement of the biopsy needle, especially if an external pressure is exerted, for example through ultrasound. The additional rotational movement about the needle's longitudinal axis can optionally be effected by the corresponding provision of the necessary measures explained above, and advantageously supports the tissue-severing process.

Following the advantageous combined movement of the biopsy needle, as described above, the gear motor 21 is reversed and the specimen-collection chamber 71 is closed through the rotation of the blade sheath, with the cutting edge 72 of the blade sheath 3 severing the tissue during the closing process. Of course, a corresponding structural modification or a corresponding control and additional elements can also effect the back-and-forth movement or the angular-rotational movement of the biopsy needle for severing the lateral specimen edges, even as the blade sheath is opening. During the closing process, the blade sheath is advanced past its closed position by about 2 mm in the direction of the needle tip. This reliably severs the tissue fibers. Afterward, the blade sheath is retracted by 2 mm into the closed position.

The microprocessor, in which the desired values are stored, effects the control of the processes; the microprocessor compares these data to the measured data (counting data), and controls the processes accordingly. The special configuration of the specimen-collection chamber 71, and the possible generation of a vacuum, hold the tissue specimen in the specimen-collection chamber 71 without rotating, so the blade sheath 3 surrounding the outside of the biopsy needle and rotating as it is longitudinally displaced does not rotate or twist the tissue specimen, as described above. After the specimen-collection chamber 71 has been closed, the DC gear motor for the vacuum-pressure-generating device 5 is activated. First the plunger 54 is retracted until it uncovers the ventilation bore (FIG. 11*c*). After the vacuum in the system has been eliminated, the plunger advances toward the bottom of the syringe until the ventilation bore is closed again, in order to prevent bodily fluid (cytological fluid) from leaking out. This brief opening of the ventilation bore is in a range of fractions of a second to avoid the entry of fluid into the hand piece. To prevent fluid from entering the hand piece via the ventilation bore or bores for safety reasons, the bores can additionally be covered with air-permeable material, so the interior of the hand piece is not contaminated. The specimen-collection diode 92 stops blinking. The ejection diode 93 illuminates yellow. The biopsy needle with the closed collection chamber is pulled out of the cannula.

d) Removing the Specimen after the Biopsy Needle Has Been Removed from the Tissue After the biopsy needle has been removed from the tissue and a container has been prepared for receiving the tissue specimen and the tissue fluid, the programming key 89 is depressed again and the ejection diode 93 begins to blink. For safety reasons, the delay circuit stipulates that the programming key must be depressed for about 1.2 to 1.5 seconds before the procedure is initiated. First, the gear motor 21 of the blade sheath is actuated in order to open the specimen-collection chamber 71 about halfway. Afterward, the DC gear motor 58 of the vacuum- and pressure-generating device is activated. The direction of rotation of the DC gear motor 58 is maintained, and the threaded spindle 53 moves, with the plunger, in the direction of the bottom of the syringe, so an overpressure now exists in the system. The plunger 54 is advanced toward the bottom of the syringe 52 and the drive motor 58 is deactivated. The gear motor 21 retracts the blade sheath further over the specimen-collection chamber 71 once the plunger has reached the bottom of the syringe 52.

Because of the overpressure that has built up in the system, the specimen is pushed out under pressure into a prepared laboratory container when the specimen-collection container is only half-open. At the same time, the hollow space of the vacuum- and pressure-generating device, the biopsy needle and the specimen-collection chamber 71 is cleared of tissue particles and fluid. The specimen is ejected when the specimen-collection chamber 71 is about half-open because this assures the ejection of the tissue specimen—it does not fall back into the specimen-collection chamber 71 due to a premature loss of the overpressure. The narrowing of the biopsy-needle hollow space by the stopper 79, which impedes or prevents the entrance of tissue into the biopsy-needle hollow space, has proven especially advantageous in specimen collection, because the narrowed cross-section increases the ejection pressure. The best ejection results were obtained with a half-open specimen-collection chamber 71, that is, when the blade sheath exposed half of the axial length of the specimen-collection chamber 71. The overpressure also pushes tissue fluid out of the specimen-collection chamber 71, and cleans it.

After the specimen-collection chamber 71 has been completely opened, and the removal and cleaning have been performed, the ejection diode goes out. The reset diode 91 illuminates yellow. Provided that no further specimens are to be collected, the housing lid is opened and the removable element 20 is removed. When the housing lid 10 is opened, the microswitch 18 deactivates the system. If, however, a further specimen is to be collected from the same area of tissue, the operator depresses the programming key 89, and the reset diode 91 begins to blink. The vacuum- and pressure-generating device 5, as well as the blade sheath, returns to the initial position.

After the procedure has been completed, the reset diode 91 goes out and the specimen-collection diode and the clamping diode illuminate (green and yellow, respectively). Now the operator must decide whether he wants to collect only one further tissue specimen from the same injection site, in which case he depresses the programming key 89, or wants to create a new injection site by clamping the biopsy needle, in which case he depresses the clamping key 90. Depending on his selection, the further process steps are performed in the order described above. The procedure can be repeated as many times as desired. After the specimen has been ejected, the operator need only decide whether he wants to collect a further specimen, or end the specimen collection and open the housing lid.

If it is necessary to collect the specimen at a site of the swelling that is not located directly above or at the specimen-collection chamber 71 following the injection—for example, it is located to the side—the knurled knob 80 can be used to rotate the position of the specimen-collection chamber 71. To allow the operator to verify the radial position of the specimen-collection chamber 71, the knurled knob is provided with a marking in the form of a notch 119, which faces up when the opening of the specimen-collection chamber 71 faces up. In the respectively set position, the biopsy needle is fixed in place by the surfaces of the polygonal member 50 and the elastic forces in the carrier part. The specimen-collection procedure is the same as described above.

After the biopsy has been completed, the lid is unlatched and the replaceable element 20 (vacuum- and pressure-generating device, biopsy needle/blade device with all elements attached thereto) is lifted up and out. To make it impossible to open the housing when the clamping carriage is clamped, a fastening panel 84 is disposed on the biopsy-needle carrier. In the clamped state, the panel rests against the left end face 85 of the closing device. The closing device, which can be displaced in the X-axis, can no longer be moved to the left into the open position, and therefore the latch 12 can no longer be removed from the recess 45. Conversely, the housing lid cannot be closed if the removable element has been inserted into the pre-clamped clamping carriage, because the fastening panel prevents the bar from being inserted into the space provided for it. The surface 85 of the bar impacts the fastening panel. The battery-charging diode 96 is shut off as soon as the housing lid is opened. When the lid is closed and the insertion element 20 is inserted, the battery-charging diode indicates whether enough power is available.

In principle, it is conceivable to control all of the steps for collecting a specimen and clamping the carriage, etc., by manually activating and deactivating the two gear motors individually. It is advantageous, however, to combine individual steps of the procedure and perform them automatically, so only the initiation of the sequence is effected by the actuation of a switch. As described above, this semi-automatic method has proven especially advantageous.

Figure 15:
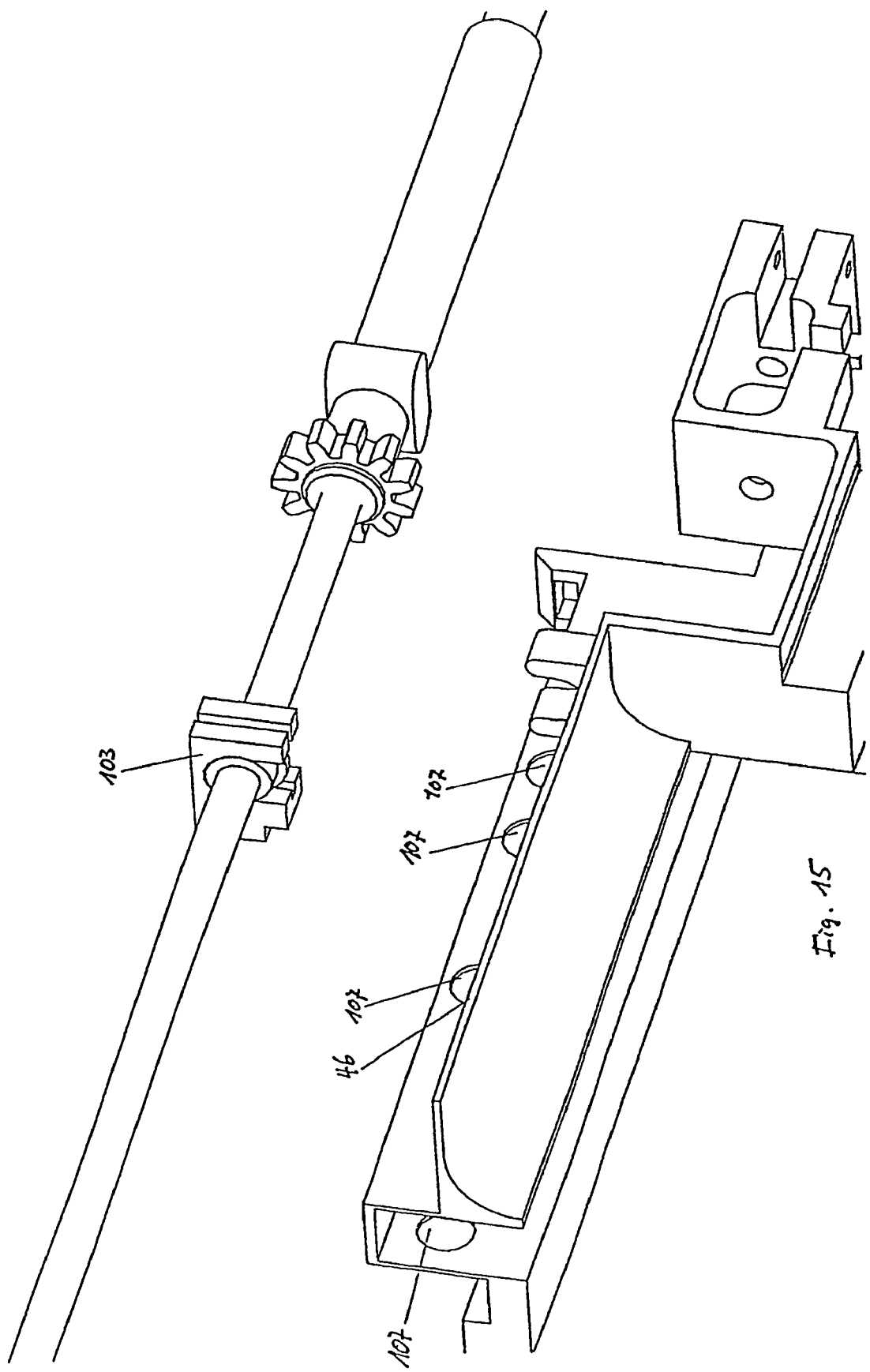
FIG. 15 depicts the base block and biopsy needle/cutting sleeve, prepared for being loaded with photocells and microswitches for measurement of actual values.

In principle, there are two conceivable methods for ascertaining the actual values for the comparison with the desired values. One method is based on measuring the longitudinal displacement of the threaded spindle during insertion or withdrawal, and measuring the axial displacement of the blade sheath or the biopsy-needle carrier. Photocells or microswitches are provided inside the housing, particularly on the extension of the base block 8, for detecting these changes. A positioning finger 103 is additionally provided on the blade sheath for photocell measurement of the changes, while the free end 61 of the threaded spindle of the vacuum- and pressure-generating device, the end protruding from the plunger unit, can be used as a measurement point. In the use of the front edge of the biopsy-needle carrier as a measurement point with a photocell, there is no need for an additional positioning finger. The recessed photocells are covered with a suitable transparent material to prevent possible contamination. The positioning finger 103 extends through a slot in the biopsy-needle holder. Recesses 107 are provided at corresponding locations on the extension 46 of the base block 8. Photocells or microswitches are installed into these recesses, and cooperate with the free end 61 of the plunger spindle, with the positioning finger, or the edge 120 of the biopsy-needle carrier (FIG. 15). These signals (actual values) are processed in the electronic components, and form the control signals.

The other system is based on measuring the rpm of the DC gear motors, which are converted into units of length; this is particularly advantageous when the gear motors effect the changes. In this instance, a detector is mounted to the shaft of the DC motor, and cooperates with a photocell mounted to the housing of the DC motor. This detector comprises a two-armed blade wheel 131 and a photocell that is connected to the motor (FIG. 3). These detectors on the two drive motors supply the counting pulses for the photocells, which transmit them further to the programmable microprocessor, which compares these ascertained data to the stored specifications and triggers the control pulses accordingly. Because the DC motors operate with an rpm of about 10,000 to 12,000, as a function of load, and the downstream planetary gear that is disposed on the power takeoff side and cooperates with the spindle drive significantly reduces the rpm, this permits a precise longitudinal control. The longitudinal displacement by the spindle drives is a consistently identical amount, proportional to the number of drive revolutions, and the number of revolutions is therefore sufficient as a control signal for the precision of the longitudinal displacement. For precisely determining the position of the blade sheath 3 and the plunger 54 at the beginning, that is, after the removable element has been inserted and the housing lid 10 has been closed, the DC gear motor 58 rotates the plunger 54 until it stops against the bottom of the syringe, and the DC gear motor 21 brings the blade-sheath drive to the zero position by bringing the gear 74 to a stop against the threaded-spindle nut 75 (the threaded-spindle nut 75 runs onto the gear 74). From this zero position, the individual steps are then controlled by comparing the settings and actual values. The necessary cables from the measurement detector to the electronic components are accommodated in the housing, as is the plate with the electronic components. If necessary, it is also possible to combine the two described control systems.

PARTS LIST

1 Handpiece
2 Biopsy needle
3 Blade sheath
4 Connecting element
5 Vacuum pressure-generating device
6 Housing end lid (left)
7 Housing end lid (right)
8 Base block
9 Lower housing part
10 Housing lid
11 Locking bar
12 Latch
13 Passageway
14 Bore
15 Passageway
16 Passageway
17 Tappet
18 Microswitch
19 Switching pin
20 Removable element
21 DC gear motor
22 Wall
23 Toothed roller
24 U-shaped space
25 Wall
26 Block
27 Groove
28 Clamping carriage
29 Threaded bore
30 Pin
31 Coil spring
32 End piece
33 Articulated lever
34 Compression spring
35 Shaft
36 Holding device
37 Biopsy-needle carrier
38 Bores
39 Legs
40 Brackets
41 Surface of clamping carriage
42 Surface extension
43 Sliding surface
44 Surface of block 26
45 Recess
46 Cover
47 Plastic part
48 Threaded-spindle nut
49 Bearing element
50 Polygonal member
51 Bottom of syringe
52 Syringe body
53 Threaded spindle
54 Plunger
55 Gear (Gear rim)
56 Drive pinion
57 Operating panel
58 DC gear motor
59 Transverse plate
60 Surfaces
61 Free end
62 Insertion element
63 Connector
64 Discharge connector
65 Recess
66 Phase
67 Ventilation bore
68 Blade (longitudinal edges)
69 Plunger/cylinder unit
70 Needle tip
71 Specimen-collection chamber
72 Blade
73 Threaded-spindle sheath
74 Gear
75 Threaded-spindle nut
76 Sealing element
77 Recesses
78 Plastic disk
79 Stopper
80 Knurled knob
81 Guide roller
82 Recess
83 Metal component
84 Fastening panel
85 End face
86

87 Center rib
88 Actuating key
89 Programming key
90 Clamping key
91 Reset diode
92 Specimen-collection diode
93 Ejection diode
94 Clamping diode
95 Locking diode
96 Battery-charging diode
97 Passageway
98 Passageway
99 Arm of two-armed lever
100 Part of lever
101 Flank of guide roller—left
102 Flank of guide roller—right
103 Positioning finger
104 Shaft
105 Drive device (vacuum)
106 Drive device (biopsy needle, clamping device)
107 Recesses
108 Brackets
109 Insertion aid
110 Pin
111 Accumulator battery
112 Plastic part
113 Surface
114 Separating plate
115 Guide bore
116 Cap element
117 Holding pieces
118 N.N.
119 Notch
120 N.N.
121 Disk insert
122 Lip
123 Collar
124 Short coil spring
125 Disk insert
126 Tubular part
127 Collar
128 Distal bore in carriage
129 Proximal-side bore in block 26
130 Photocell
131 Blade wheel
0 Deformed point
S Inscribed circle diameter
A Clear spacing
X Proximal displacement
X Distal displacement
   Rotational angle—right
   Rotational angle—left
H Height of specimen-collection chamber
F Height of opening
$T_1$ Partial piece
ra Outside diameter
ri Inside diameter

The invention claimed is:

1. A biopsy device for tissue collection, comprising:
a housing containing a power source; and
a removable element, comprising a biopsy needle module, a pressure source and a hollow connecting element, the biopsy needle module having a biopsy needle, a cutting sleeve and a biopsy needle carrier to which the biopsy needle and the cutting sleeve are mounted, wherein the removable element is configured for insertion into the housing with both the pressure source and the biopsy needle carrier being contained within the housing and with the pressure source and the biopsy needle carrier being spaced apart within the housing, and the hollow connecting element coupled as a fluid coupling between the biopsy needle module and the pressure source;
wherein the housing includes a lower housing segment, a housing lid coupled to the lower housing segment, a first end lid and a second end lid, each of the first end lid and the second end lid being connected to the lower housing segment, wherein the second end lid comprises a first U-shaped opening and a second U-shaped opening, wherein the first U-shaped opening is configured to receive a first portion of the removable element and the second U-shaped opening is configured to receive a second portion of the removable element, and wherein a third portion of the removable element is located between the first U-shaped opening and the second U-shaped opening external to the housing; and
wherein the first end lid comprises a third U-shaped opening at the top thereof, and the third U-shaped opening is configured to receive a portion of the removable element.

2. The biopsy device according to claim 1, the biopsy needle comprising a sharpened distal end and a distal opening for collection of tissue, the cutting sleeve having a cutting blade on the distal end thereof and coaxially positioned with respect to the biopsy needle.

3. The biopsy device according to claim 2, wherein the pressure source comprises a vacuum pressure-generating device having a piston/cylinder arrangement, the vacuum pressure-generating device being connected to a proximal end of the biopsy needle via the hollow connecting element.

4. The biopsy device according to claim 2, further comprising a clamping cradle contained within the housing and a drive unit contained within the housing, the clamping cradle connected to the drive unit.

5. The biopsy device according to claim 4, wherein the biopsy needle module is configured to be connected to the clamping cradle such that the biopsy needle module is longitudinally displaceable by the clamping cradle.

6. The biopsy device according to claim 5, wherein the cutting sleeve is connected to the drive unit, the cutting sleeve being configured to be axially movable relative to the biopsy needle.

7. The biopsy device according to claim 5, wherein the clamping cradle is configured to cause the biopsy needle to penetrate into a patient a predetermined distance upon actuation of the clamping cradle.

8. The biopsy device according to claim 7, wherein the clamping cradle is configured to be set to a plurality of penetration distances for the biopsy needle.

9. The biopsy device according to claim 7, wherein the clamping cradle is configured to be set to a penetration distance for the biopsy needle which is in the range between approximately 15 mm and 25 mm.

10. The biopsy device according to claim 4, wherein a locking mechanism is contained within the housing to lock the clamping cradle, the locking mechanism comprising a handle with an arm, wherein the arm is configured to lock into a depression in the clamping cradle.

11. The biopsy device according to claim 10, wherein the clamping cradle is comprised of a plastic material and the arm is comprised of a metal.

12. The biopsy device according to claim 1, wherein the power source comprises at least one battery.

13. The biopsy device according to claim 1, wherein the lower housing segment has lateral walls of different heights.

14. The biopsy device according to claim 1, further including a guide disposed on the removable element, and wherein the third U-shaped opening is sized to receive the guide of the removable element.

15. The biopsy device according to claim 1, further comprising a control panel attached to the housing, wherein the control panel is connected to the power source.

16. The biopsy device according to claim 15, wherein the control panel is connected to a circuit board.

17. The biopsy device according to claim 16, wherein the circuit board has a programmable microprocessor disposed thereon.

18. The biopsy device according to claim 16, wherein the control panel comprises a control key configured to actuate a clamping cradle, a program key configured to actuate a tissue sampling procedure and a clamping key configured to trigger clamping of the clamping cradle.

19. The biopsy device according to claim 18, wherein the program key is positioned between the control key and clamping key to avoid accidental actuation of the clamping cradle.

20. The biopsy device according to claim 18, wherein each of the keys has a light associated therewith that is configured to indicate whether the key is active.

21. The biopsy device according to claim 18, wherein the clamping key is equipped with a delay circuit.

22. The biopsy device according to claim 1, wherein the housing lid further comprises a longitudinally displaceable locking mechanism.

23. A biopsy device for tissue collection, comprising:
a housing containing a power source, wherein the housing comprises a lower housing segment with lateral walls, a housing lid matched to the lower housing segment and having a longitudinally displaceable locking mechanism mounted to the housing lid and configured to engage a fastening device on the lower housing segment, and a first end lid and a second end lid, each of the first end lid and the second end lid being connected to the lower housing segment;
a removable element, comprising a biopsy needle module, a pressure source and a hollow connecting element, the biopsy needle module having a biopsy needle, a cutting sleeve and a biopsy needle carrier to which the biopsy needle and the cutting sleeve are mounted, wherein the removable element is configured for insertion into the housing with both the pressure source and the biopsy needle carrier being contained within the housing and with the pressure source and the biopsy needle carrier being spaced apart within the housing, and the hollow connecting element coupled as a fluid coupling between the biopsy needle module and the pressure source;
wherein the second end lid comprises a first U-shaped opening and second U-shaped opening, wherein each of the first U-shaped opening and the second U-shaped opening is configured to receive a respective portion of the removable element, with at least a portion of the hollow connecting element being located between the first U-shaped opening and the second U-shaped opening external to the housing; and
wherein the first end lid comprises a third U-shaped opening at the top thereof, the third U-shaped opening sized to receive a portion of the removable element.

24. A biopsy device for tissue collection, comprising:
a housing including a lower housing segment, a housing lid coupled to the lower housing segment, a first end lid, and a second end lid, each of the first end lid and the second end lid being connected to the lower housing segment, wherein the second end lid has a first U-shaped opening and a second U-shaped opening, and the first end lid has a third U-shaped opening;
a unitary removable element including a biopsy needle module, a pressure source, and a hollow connecting element coupled as a fluid coupling between the biopsy needle module and the pressure source; and
the unitary removable element being configured to be mounted to the housing and received at each of the first U-shaped opening, the second U-shaped opening and the third U-shaped opening, with the pressure source being contained within the housing, and with at least a portion of the hollow connecting element being external to said housing in a region between the first U-shaped opening and the second U-shaped opening to establish a fluid path that extends between the first U-shaped opening and the second U-shaped opening external to the housing.

25. The biopsy device of claim 24, wherein the biopsy needle module includes a first portion configured to be received by the first U-shaped opening and the pressure source includes a second portion configured to be received by the second U-shaped opening.

26. The biopsy device of claim 25, wherein the first portion is a round profile portion of the biopsy needle module and the second portion is a nozzle portion of the pressure source.

27. The biopsy device of claim 26, wherein the biopsy needle module includes a biopsy needle and a cutting sleeve coaxially positioned with respect to the biopsy needle, the biopsy needle module further including a guide roller slidably disposed on said cutting sleeve, the guide roller configured for being slidably received by the third U-shaped opening to maintain a position of the guide roller.

28. The biopsy device of claim 26, wherein the biopsy needle module includes a biopsy needle configured to extend outwardly from the housing from the third U-shaped opening, and wherein the fluid path is configured to further extend within the housing through the biopsy needle module between the first U-shaped opening and the third U-shaped opening.

29. The biopsy device of claim 24, wherein the fluid path is configured to further extend through an interior of the housing between the first U-shaped opening and the third U-shaped opening by way of the biopsy needle module.

* * * * *